(12) United States Patent
Baker et al.

(10) Patent No.: US 10,383,646 B2
(45) Date of Patent: Aug. 20, 2019

(54) METHODS AND SYSTEMS FOR DELIVERY OF ACOUSTIC ENERGY TO TISSUE SURFACES, CAVITIES AND OBSTRUCTED PASSAGES SUCH AS INTRANASAL OSTIA

(75) Inventors: Peter Christensen Baker, San Anselmo, CA (US); Richard Treadwell, Tartegnin (CH)

(73) Assignee: Sanovas Intellectual Property, LLC, Reno, NV (US)

( * ) Notice: Subject to any disclaimer, the term of this patent is extended or adjusted under 35 U.S.C. 154(b) by 460 days.

(21) Appl. No.: 13/160,858

(22) Filed: Jun. 15, 2011

(65) Prior Publication Data

US 2011/0282251 A1 Nov. 17, 2011

Related U.S. Application Data

(63) Continuation-in-part of application No. PCT/US2009/068309, filed on Dec. 16, 2009.
(Continued)

(51) Int. Cl.
*A61M 3/02* (2006.01)
*A61B 17/24* (2006.01)
(Continued)

(52) U.S. Cl.
CPC .......... *A61B 17/24* (2013.01); *A61M 3/0275* (2013.01); *A61M 11/005* (2013.01); *A61M 15/08* (2013.01); *A61M 16/0434* (2013.01); *A61M 16/0461* (2013.01); *A61M 19/00* (2013.01); *A61M 31/00* (2013.01); *A61M 37/0092* (2013.01); *A61B 2017/246* (2013.01);
(Continued)

(58) Field of Classification Search
CPC .............................. A61N 7/00; A61H 23/0245
USPC ............................................................. 601/2
See application file for complete search history.

(56) References Cited

U.S. PATENT DOCUMENTS

| 4,776,990 A | 10/1988 | Verity |
| 4,805,614 A | 2/1989 | Lerner |

(Continued)

FOREIGN PATENT DOCUMENTS

| WO | 1997/017933 A1 | 5/1997 |
| WO | 2007/129297 A2 | 11/2007 |

OTHER PUBLICATIONS

Ansari, Noureddin Nakhostin PhD, PT et al., "A preliminary study into the effect of low-intensity pulsed ultrasound on chronic maxillary and frontal sinusitis," Physiotherapy Theory and Practice, vol. 23, No. 4, pp. 211-218 (2007).
(Continued)

*Primary Examiner* — Hien N Nguyen
(74) *Attorney, Agent, or Firm* — Forge IP, PLLC

(57) ABSTRACT

Methods and systems for delivering fluids, aerosols, and/or acoustic energy to target sites on tissue surfaces and within body cavities or lumens, obstructions or undesired materials associated with body cavities and tissue surfaces and, particularly, target sites on tissue surfaces or at obstructions within natural orifices, such as ear, nose and throat passages and, particularly, nasal passages and cavities, are provided. Delivery of acoustic energy may be accomplished using a flexible, expandable member adapted to be expanded at a target site using an acoustically transmissive material for delivery of acoustic energy to tissue surfaces in irregularly configured tissue cavities and passageways.

25 Claims, 23 Drawing Sheets

Related U.S. Application Data

(60) Provisional application No. 61/138,077, filed on Dec. 16, 2008, provisional application No. 61/138,083, filed on Dec. 16, 2008, provisional application No. 61/138,096, filed on Dec. 16, 2008.

(51) Int. Cl.

| *A61M 11/00* | (2006.01) |
|---|---|
| *A61M 15/00* | (2006.01) |
| *A61M 15/08* | (2006.01) |
| *A61M 16/04* | (2006.01) |
| *A61M 19/00* | (2006.01) |
| *A61M 31/00* | (2006.01) |
| *A61M 37/00* | (2006.01) |

(52) U.S. Cl.
CPC ... *A61M 15/0085* (2013.01); *A61M 2205/051* (2013.01); *A61M 2205/057* (2013.01); *A61M 2205/058* (2013.01); *A61M 2205/3368* (2013.01); *A61M 2205/3606* (2013.01); *A61M 2205/8206* (2013.01); *A61M 2205/8243* (2013.01); *A61M 2210/065* (2013.01); *A61M 2210/0618* (2013.01); *A61M 2210/0625* (2013.01); *A61M 2210/0662* (2013.01); *A61M 2210/0681* (2013.01)

(56) References Cited

U.S. PATENT DOCUMENTS

| 5,827,024 | A | 10/1998 | Grandia et al. |
|---|---|---|---|
| 5,989,208 | A | 11/1999 | Nita |
| 6,312,383 | B1 | 11/2001 | Lizzi et al. |
| 6,478,754 | B1 | 11/2002 | Babaev |
| 6,569,099 | B1 | 5/2003 | Babaev |
| 6,601,581 | B1 | 8/2003 | Babaev |
| 6,623,444 | B2 | 9/2003 | Babaev |
| 6,685,657 | B2 | 2/2004 | Jones |
| 6,692,450 | B1 | 2/2004 | Coleman |
| 6,907,879 | B2 | 6/2005 | Drinan et al. |
| 7,073,500 | B2 | 7/2006 | Kates |
| 7,128,897 | B2 | 10/2006 | Osbakken et al. |
| 7,186,234 | B2 | 3/2007 | Dahla et al. |
| 7,191,780 | B2 | 3/2007 | Faram |
| 7,297,131 | B2 | 11/2007 | Nita |
| 7,431,704 | B2 | 10/2008 | Babaev |
| 7,494,468 | B2 | 2/2009 | Rabiner et al. |
| 7,500,971 | B2 | 3/2009 | Chang et al. |
| 7,522,955 | B2 | 4/2009 | Rontal |
| 7,959,597 | B2 | 6/2011 | Baker et al. |
| 2002/0019627 | A1 | 2/2002 | Maguire et al. |
| 2002/0138036 | A1 | 9/2002 | Babaev |
| 2003/0092667 | A1* | 5/2003 | Tachibana .......... A61K 41/0047 514/44 A |
| 2004/0024402 | A1 | 2/2004 | Nita |
| 2004/0054363 | A1* | 3/2004 | Vaska ...................... A61N 7/02 606/27 |
| 2004/0073178 | A1* | 4/2004 | Anderson et al. ............ 604/275 |
| 2004/0204728 | A1 | 10/2004 | Haefner |
| 2005/0075621 | A1 | 4/2005 | Rontal |
| 2005/0080359 | A1 | 4/2005 | Zhao et al. |
| 2005/0080396 | A1 | 4/2005 | Rontal |
| 2006/0210605 | A1 | 9/2006 | Chang et al. |
| 2006/0224103 | A1 | 10/2006 | Rontal |
| 2007/0202051 | A1 | 8/2007 | Schuschnig |
| 2007/0244529 | A1* | 10/2007 | Choi et al. ...................... 607/96 |
| 2007/0256686 | A1 | 11/2007 | Lerner et al. |
| 2007/0267011 | A1* | 11/2007 | Deem et al. ............. 128/200.23 |
| 2007/0299396 | A1 | 12/2007 | Rocklin |
| 2008/0027423 | A1 | 1/2008 | Choi et al. |
| 2008/0031094 | A1* | 2/2008 | Laugharn et al. ............ 367/138 |
| 2008/0154183 | A1 | 6/2008 | Baker et al. |
| 2008/0262489 | A1* | 10/2008 | Steinke ........................... 606/33 |
| 2009/0142277 | A1 | 6/2009 | Osbakken et al. |
| 2009/0163890 | A1 | 6/2009 | Clifford et al. |
| 2009/0177123 | A1 | 7/2009 | Peterson |
| 2009/0281483 | A1 | 11/2009 | Baker et al. |
| 2010/0022919 | A1 | 1/2010 | Peterson |
| 2010/0076269 | A1 | 3/2010 | Makower et al. |
| 2010/0174308 | A1 | 7/2010 | Chang et al. |
| 2010/0316576 | A1 | 12/2010 | Keller et al. |

OTHER PUBLICATIONS

Ansari, Noureddin Nakhostin et al., "Physiotherapy for chronic rhinosinusitis: The use of continuous ultrasound," International Journal of Therapy and Rehabilitation, vol. 14, No. 7, pp. 306-310 (Jul. 20074).

Ansari, Noureddin Nakhostin, et al., "Therapeutic ultrasound as a treatment for chronic sinusitis," Physiotherapy Research International, vol. 9, No. 3, pp. 144-146 (2004).

Chongqing Haifu(HIFU) Technology Co Ltd., "The Haifu System" Product Sheet, http://www.haifu.com.cn/en_about.asp?, 3 pages (Oct. 16, 2008).

Arthocare ENT, "Treatment of Turbinate Reduction Tehnique Guide and Roundtable Discussion," www.arthocareENT.com, 6 pages (2006).

Celleration, Inc., "MIST Therapy System," Product Brochure, http://www.celleration.com, 5 sheets, (Feb. 27, 2008).

\* cited by examiner

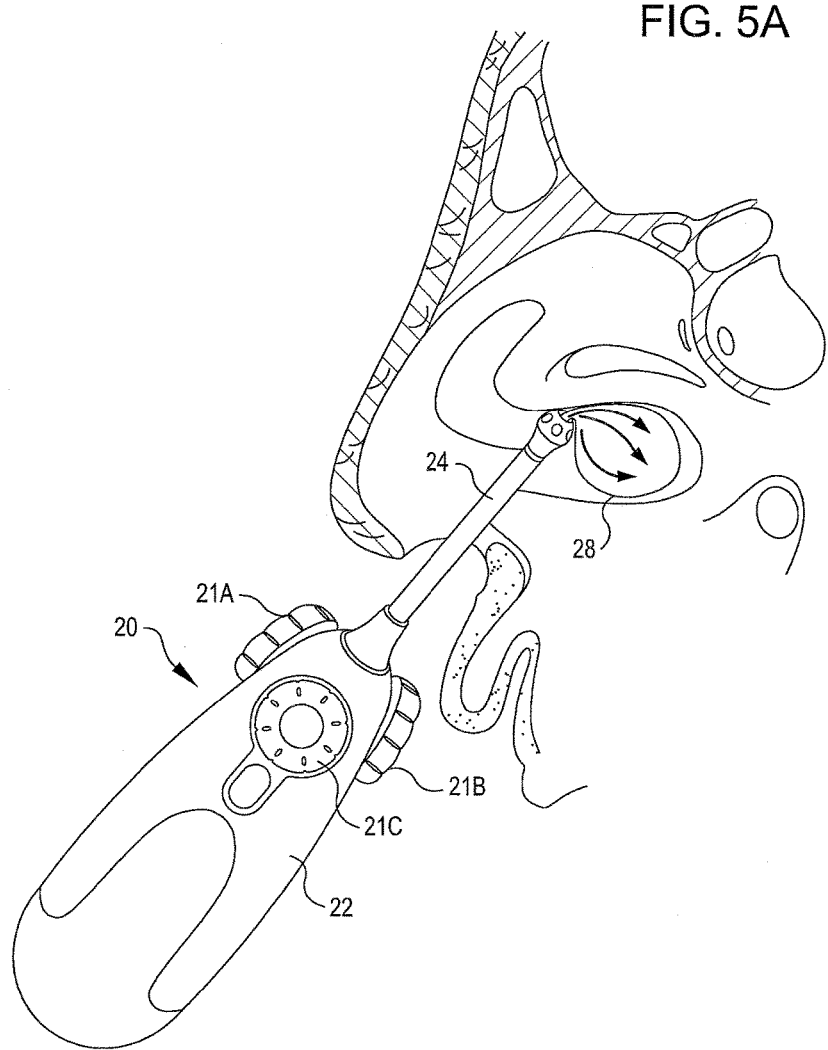

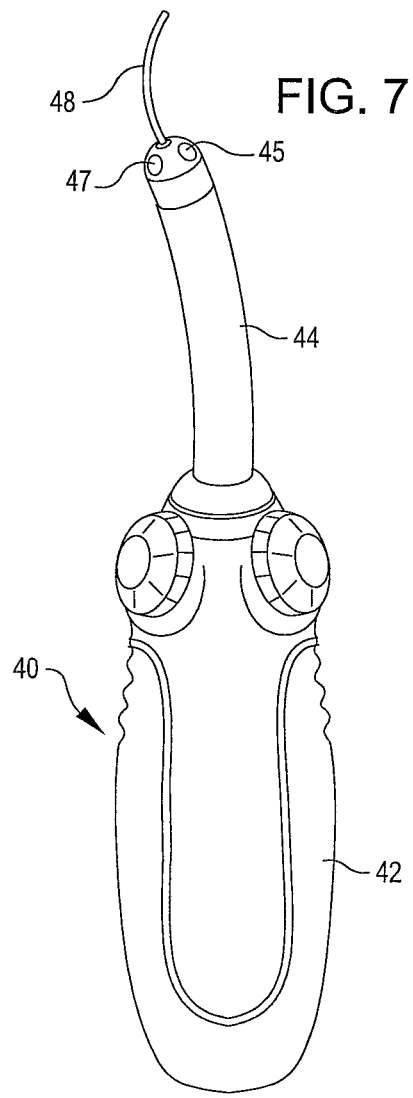

METHODS AND SYSTEMS FOR DELIVERY OF ACOUSTIC ENERGY TO TISSUE SURFACES, CAVITIES AND OBSTRUCTED PASSAGES SUCH AS INTRANASAL OSTIA

REFERENCE TO RELATED APPLICATIONS

This patent application is a continuation-in-part application of PCT International Application No. PCT/US2009/068309 filed Dec. 16, 2009, which claims priority to U.S. provisional patent application Nos. 61/138,077, 61/138,083 and 61/138,096, all filed Dec. 16, 2008.

TECHNICAL FIELD

The present invention relates to methods and systems for delivering fluids, aerosols, and/or acoustic energy to tissue surfaces, body cavities or lumens, obstructions or undesired materials associated with body cavities or passageways, or on tissue surfaces. In one aspect, the present invention relates to methods and systems for delivering fluids and/or aerosols to tissue sites at generally high frequency (e.g., sonic and/or ultrasound) pulsation rates. In another aspect, the present invention relates to methods and systems for delivering acoustic energy (e.g., sonic and/or ultrasound energy, and including high intensity ultrasound (HIU) and high intensity focused ultrasound (HIFU)) directly to tissue, or to obstructions in passages or cavities such as nasal passages, sinuses and sinus ostia. In another aspect, methods and systems of the present invention are employed with catheter systems to deliver fluids, aerosols, and/or acoustic energy to tissue surfaces, body cavities or lumens, obstructions or undesired materials at internal body sites using minimally invasive interventional catheters.

BACKGROUND

Rhinitis is produced by irritation and inflammation of the mucous membranes of the nasal cavities and is generally caused by allergic reactions, environmental irritants, bacteria and/or viruses. Symptoms of rhinitis include ninny nose, nasal congestion and post-nasal drip. Rhinitis has been associated not only with discomfort, congestion and nasal conditions, but also sleeping problems, ear conditions and learning challenges. Treatment generally involves administration of antihistamines, leukotriene antagonists, nasal corticosteroids, decongestants, allergen immunotherapies, or saline irrigation of sinus cavities.

Sinusitis is produced by a number of pathologic processes, including inflammation of the sinus cavities, poor mucus transport, obstruction of passages from inflammatory debris and growth of biofilms within the sinuses and their drainage systems (ostea). Additionally, resulting stagnation, edema and poor blood flow in the surrounding tissue further decreases the ability of blood borne assistance in the form of immune modulators and antibiotics to reach the site. Microorganisms encased in biofilms are notoriously difficult to treat, since the biofilm matrix is highly resistant both to the action of the immune system and to treatment with antibiotics. Sinusitis therapy may involve saline irrigation and administration of aerosols, as well as the administration of drugs such as antibiotics, decongestants, antihistamines and nasal steroids, sinus surgery, balloon sinuplasty and administration of nebulized antibiotics. Response rates for current therapies are generally relatively low, both on a short term and a long term basis. This is likely because of the multifactorial nature of this disease as described above. Each individual therapy used as standard treatment for sinusitis does not address all pathophysiologic causes that accumulate to cause the disease, sinusitis. This is true for other diseases such as chronic ear infections, recurrent skin infections, chronic wounds, vascular plaques, gastroenterologic obstructions and solid tumors.

Nasal irrigators for application of both solutions and aerosols are well known and are used to relieve symptoms of sinusitis and rhinitis, such as nasal congestion. Routine nasal irrigation generally improves symptoms in adults with chronic rhinosinusitis, as well as children with allergic rhinitis. Irrigating fluid, such as saline, may improve nasal ciliary motility and may additionally reduce airway edema and soften the mucus, which allows more effective aspiration. Irrigation and aspiration, or suctioning, is typically performed in hospital or medical office environments using installed, wall suction systems that are quite powerful and can be quite effective. Manual irrigating and/or aspirating devices that are available for home use are generally low flow rate, low aspiration pressure devices. Neti pots and squeeze bottles, for example, are used to irrigate nasal passageways manually and, while they temporarily relieve symptoms, they provide little long term comfort.

US 2008/0154183 A1 discloses self-contained, motorized devices that provide continuous or intermittent suction, as well as continuous or intermittent, on-demand delivery of irrigating fluid to nasal passages. US 2009/0281454 A1, 2009/0281482 A1, 2009/0281483 A1 and 2009/0281485 A1 disclose additional features of irrigation and aspiration devices. The disclosures of these patent publications are incorporated herein by reference in their entireties.

Commercial devices provide pulsed mist and/or a pulsating rinse to nasal passages using misting wands. Recent product improvements include a flex tip allowing 360° rotation with a tip locking and release feature, variable, stepless pressure control and a calibrated pulse rate. Different wands may be provided for the pulsed mist and pulsating rinse modes.

Delivery of liquid rinses and mists to nasal passages is described in the patent literature. US 2007/0299396 A1 discloses a pulsatile irrigation device producing a calibrated pulsatile rinse of 1200-1250 pulses/min, driven by a piston driven pump assembly. Atomization to droplets of about 15-25 microns is accomplished using a bolt encased in the end of the tip. U.S. Pat. Nos. 4,776,990, 4,805,614 and WO 2007/129297 disclose devices for home and office use that provide water-saturated, pressurized, heated air to nasal passages.

Many different types of nebulizers and aerosol generators have been developed. Some devices employ ultrasound transducers to nebulize solutions or generate aerosol droplets. U.S. Pat. No. 3,774,602, for example, discloses a disposable, cartridge-type single shot ultrasonic nebulizer for inhalation therapy. U.S. Pat. No. 4,109,863 discloses another apparatus for ultrasonic nebulization of liquid samples or suspensions. U.S. Pat. No. 4,319,144 discloses a nebulization control system for a piezoelectric ultrasonic nebulizer. U.S. Pat. No. 6,357,671 discloses another ultrasonic nebulizer that is controllable to vary the amplitude of the ultrasonic output.

Liquid aerosols may also be produced using micropumps, including electronic micropumps. In one system, a dome-shaped aperture plate or diaphragm having many tapered holes is vibrated at a high rate (e.g., 100,000 times per second). The rapid vibration causes each aperture to act as a micropump, drawing liquid through the holes and ejecting consistently sized droplets.

Liquid projection apparatus having addressable nozzles are also known. U.S. Pat. No. 6,394,363 discloses a device having multiple transducers associated with multiple nozzles for projecting liquid as jets or droplets from selected nozzles. Related liquid projection apparatus are described in PCT International Publications WO 2008/044069 A1, WO 2008/044070 A1, WO 2008/0044071 A1, WO 2008/0044072 A1 and WO 2008/0044073 A1.

Application of ultrasound directly or indirectly to the nasal passages, or to tissue in the nasal passages, has also been proposed. Experimental studies administering low intensity (1 W/cm$^2$), pulsed (1:9) and continuous therapeutic ultrasound at a frequency of 1 MHz to sinuses by application of an ultrasound soundhead to the skin of the cheeks and forehead were conducted to ascertain the effect on chronic sinusitis and chronic rhinosinusitis. Ansari et al., Therapeutic ultrasound as a treatment for chronic sinusitis, *Physiotherapy Research International*, 9(3) 144-146 (2004); Ansari et al., Physiotherapy for chronic rhinosinusitis: The use of continuous ultrasound, *International Journal of Therapy and Rehabilitation*, July 2007, Vol. 14, No. 7; Ansari et al., A preliminary study into the effect of low-intensity pulsed ultrasound on chronic maxillary and frontal sinusitis, *Physiotherapy Theory and Practice*, 23(4):211-218, 2007.

The use of high intensity focused ultrasound (e.g., HIFU) is well known for ablation or remodeling of various types of tissue. Ultrasound catheter systems for delivering ultrasound energy for ablating obstructions within blood vessels using an ultrasound transmission wire or ultrasound transmission member are described, for example, in U.S. Pat. Nos. 7,297,131 and 5,989,208.

A handheld, focused ultrasonic therapeutic device for treating skin lesions involved with gynecological disorders is described in US 2005/0080359. A supersound treatment apparatus suitable for treatment of rhinitis is described in PCT International Patent Publication WO 2008/009186. Devices targeting ultrasound beams on subepithelial layers of nasal mucosa in the nasal turbinates have been reported to reduce the volume of inferior turbinates, while increasing the volume of nasal ventilation.

US 2008/0027423 discloses a system for treatment of nasal tissue by application of ultrasound energy directly to tissue regions beneath the surface of the turbinate tissue. Fluid may be infused or injected directly into the turbinate tissue being treated, e.g. to enlarge the size of the turbinates and ensure delivery of ultrasound energy directly to the tissue. U.S. Patent Publications 2007/0244529 and 2008/0027423 relate to injecting fluid into the nasal turbinate using retractable needles at the end of a wand and then delivering ultrasound energy into the turbinate tissue. The treatment is accomplished using frequencies of from 0.5 to 12 MHz, generally from 5 to 12 MHz. Cooling fluid and/or radio frequency (RF) energy may also be delivered from the ultrasound and infusion probe.

Other modalities, including surgical techniques, are also used for treating tissue in intranasal passages. Somnoplasty uses controlled, low-power radiofrequency energy to create one or several submucosal volumetric lesions, which are resorbed over a period of several weeks to reduce unwanted tissue volume and stiffen remaining tissue in desired areas. Electrosurgical techniques are used for ablating, shrinking, coagulating or otherwise modifying tissue, including enlarged or hypertrophied nasal turbinates. In some systems, an active electrode of an electrosurgical probe is positioned in proximity to target tissue in the presence of an electrically conductive fluid. When a high frequency voltage is applied, tissue in proximity to the electrode is ablated, severed, or modified. Endoscopic techniques such as balloon sinuplasty, in which a sinus balloon catheter is positioned across a blocked ostium and inflated to restructure the blocked ostium, are also used for opening blocked passageways. Placement of stents and other implantable devices in sinus passageways is also performed to maintain patency.

Rhinitis and sinusitis remain widespread throughout many populations despite the many devices and systems described in the prior art. Effective and long-lasting reduction of mucus and accumulated inflammatory debris and reduction in the growth of biofilms within the nasal passages, sinuses and their drainage systems, remain challenging despite the proliferation of treatment options. There is a basis for using both saline and ultrasound individually for the treatment of nasal congestion, chronic sinusitis and chronic wounds. The disclosure presented herein is directed, in part, to providing improved methods and systems for delivery of fluids and aerosols and ultrasound energy to tissue surfaces, cavities and obstructed sites in passages, lumens or cavities such as nasal passages, sinuses and sinus ostia.

SUMMARY

There is a basis for using saline and ultrasound, individually, for the treatment of nasal congestion, chronic sinusitis and chronic wounds. The applicants have discovered, unexpectedly, that using saline and other fluids and aerosols in combination with high frequency acoustic energy, or administering fluids and aerosols by pulsation at high frequencies, such as ultrasound frequencies, provides a synergistic effect. Methods and systems of the present invention thus, in one aspect, employ the application of acoustic energy, such as generally high frequency (e.g., sonic and/or ultrasound) acoustic energy, directly and/or through the delivery of pulsed irrigation fluids and/or aerosol flows, to address a range of pathophysiological processes that accumulate, and interact, to cause various illnesses and conditions, and to produce undesired symptoms.

Methods and systems of the present invention may be applied for the treatment of tissue sites such as skin surfaces, organs and internal tissue surfaces, and to obstructions on tissue surfaces or within body cavities, lumens or the like, for disruption and/or removal of the obstruction(s). The systems may incorporate a guidable insertion wand for use in connection with external skin surfaces and tissues within natural orifices, while a catheter-based system may be used for accessing desired internal tissue sites. Some embodiments involve the delivery of acoustic energy directly to tissue or to obstructions, or delivery of pulsed irrigation fluids and/or aerosol flows, and employ multiple modes of administration, such as delivery of acoustic energy and/or irrigation fluid(s) or aerosol(s) at multiple frequencies (e.g. ultrasound and/or sub-ultrasound frequencies), intensities, pulse durations, pulse repetition rates, duty cycles, and the like. Yet other embodiments involve the administration of acoustic energy, or delivery of pulsed irrigation fluids and/or aerosol flows, according to single or multiple modes of operation, in combination with another treatment modality such as administration of an antimicrobial or therapeutic agent, application of electromagnetic radiation, an electrical field, radio frequency energy, laser energy, microwave energy, or the like.

In one aspect, methods and systems of the present invention produce a liquid stream and/or aerosol particles and/or aerosol droplets and deliver the liquid and/or aerosol to a tissue surface, or to a cavity or lumen or an obstruction, at generally high frequency pulsations (generally >1500 Hz) in "sonic" (sub-ultrasound) and/or ultrasonic frequency range(s) and at a generally low pressure. The tissue surface may be an external tissue surface, such as a skin surface or a wound, or it may be a tissue surface in a body cavity or lumen, such as in the vascular system, the respiratory system, the gastrointestinal system, the reproductive system, or a natural orifice such as the mouth and/or throat, the ear, the nose, including the nasal cavity and nasal passageways. The obstruction may be an obstruction in a body cavity, such as a nasal cavity or passageway or in another natural orifice, or at another internal or external body location and may comprise pathological tissue, cellular debris, or the like. The aerosol may comprise a suspension of fine solid particles, or liquid droplets, or a mixture of solid particles and liquid droplets, and it may be generated using a variety of systems known in the art for generating aerosols.

In some embodiments, delivery of an irrigating liquid and/or aerosol may be accomplished using multiple and/or alternating pulsations having different frequencies, intensities, pulse durations, pulse repetition rates and/or duty cycles. Pulsed delivery using generally high frequency pulsations, or alternating pulsations of different frequencies, may preferentially provide cavity entry (e.g., by Helmholtz principle), biofilm dissolution or reduction, degradation of pathological tissue, acoustic enhancement of delivery of medications or other treatment modalities, improvement of circulation, local immune modulation, and other desired effects. Different operating modalities providing delivery of acoustic energy at multiple frequencies may be provided, and may be selectable by the user, to preferentially promote various functionalities.

Liquid streams and aerosol droplets delivered to tissue surfaces such as skin, natural orifice cavities such as intranasal passages, and to obstructions at a variety of tissue sites by means of generally high frequency pulsations are preferably aqueous and inactive compositions dissolved in or carried by the saline). Liquid streams and aerosol droplets delivered using high frequency pulsations may alternatively, or additionally, comprise saline or another carrier solution comprising antibiotics, antimicrobial agents, drugs, or the like, dissolved or suspended in the liquid solution and/or delivered as aerosol particles or droplets. Suitable medications for delivery in a liquid stream or as aerosol particles or droplets may comprise (and are not limited to), in addition to saline, hypertonic saline, lactated ringer's solution, dead sea salt solution, antibiotics, midazolam, fentanyl, insulin, growth hormone, one or more growth factors, gentamycin, clindamycin, ciprofloxacin, cefuroxime, cancer treatment compositions such as cancer chemotherapeutic agents, levofloxocin, tobramycin, ampicillin+sulbactam, amphotericin, tobramycin/amphotericin combinations, cefotaxime, ceftriaxone, fluticasone, budesonide, synthetic antimicrobial molecules such as agangiocides, mometasone furoate monohydrate, xylitol, eucalyptus, tea tree oil, capsaicin, grapefruit seed extract, oil of wintergreen, and the like.

Devices of the present invention for delivery of an irrigating liquid and/or aerosol to a desired site on the skin or within the respiratory system or a natural orifice are generally handheld devices comprising a handle and at least one solution and/or aerosol discharge port. Source liquid for discharging onto tissue surfaces, or for generation of aerosol droplets, may be stored in a reservoir or device assembly separate from the handheld device and provided to the handheld device using appropriate tubing, conduits, and the like. Alternatively, devices of the present invention may incorporate a refillable liquid reservoir for storing source liquid, or mate with a disposable cartridge or liquid reservoir that may be provided in a pre-filled or tillable format and is attachable to and detachable from the device, generally at the handle portion. Device features and configurations, including irrigation and aspiration features, nozzle features, dual function switch features, articulating head features, pump and fluid control features and aspiration features may be similar to those described in U.S. Patent Publications 2008/0154183 A1, US 2009/0281454 A1, 2009/0281482 A1, 2009/0281483 A1 and 2009/0281485 µl, the disclosures of which are incorporated herein by reference in their entireties.

In another aspect, methods and systems of the present invention deliver generally high frequency (e.g., ultrasound) acoustic energy for application directly to tissue surfaces or to obstructions within body cavities or lumens, including blocked sites or obstructions in orifices or lumens such as in nasal passages. In one embodiment, devices of the present invention comprise an insertion wand sized and configured for insertion into at least a portion of a body cavity or lumen, or for contacting a target site on a tissue surface or at an obstruction within a body cavity or lumen, and an acoustic energy delivery member associated with the insertion wand for conveying generally high frequency acoustic energy (e.g., ultrasound energy, including high intensity ultrasound (HIU) and high intensity focused ultrasound (HIFU)) directly to tissues or obstructed sites, such as within nasal passages.

In another embodiment, an acoustic energy deliver member such as an extendable to and retractable wire, or another guidable structure, may be provided for delivering generally high frequency acoustic energy to tissue sites. This type of energy delivery member may be positioned in and across cavities, passageways or other body orifices that are pathologically narrowed (e.g., sinus ostia, osteomeatal complexes, vessels and lumens, portions of the gastrointestinal tract, and the like), providing delivery of energy, such as acoustic energy, to enlarge cavities and passageways and restore proper function.

In another embodiment, a deformable expandable member, such as a balloon, may be provided and expanded at a desired site, such as an internal cavity or passageway, by fluid delivery to the expandable member. The deformable walls of the expandable member may thus be positioned in proximity to or in contact with the walls of internal cavities and/or passageways having various configurations. Energy, such as high frequency acoustic energy, may be delivered through the fluid contained within the expandable member and through the walls of the expandable member to the walls of the internal cavities and/or passageways and neighboring tissues.

Delivery of high frequency acoustic energy provides mechanical and cavitational effects that promote opening of blocked passages and lumens, such as nasal passages, sinuses and sinus ostia. High frequency, generally high intensity acoustic energy may be provided directly to an obstructed site, such as an intranasal passage or another body lumen or cavity, to preferentially disrupt and/or ablate pathological tissue, obstructions, cellular debris and the like, including inflammatory buildup, bony hypertrophy, various types of plaque, and biofilms.

In some embodiments, delivery of acoustic energy at particular frequencies, intensities, pulse durations, pulse repetition rates, and/or duty cycles, may be selected to promote effects such as immune modulation, improved vascularization, bioacoustic effects and improved efficacy of administered agents such as antibiotic, antimicrobial and other agents. Systems and methods of the present invention may also provide delivery of one or more predetermined sequences of acoustic energy, with each sequence providing delivery of acoustic energy at a different frequency, intensity, pulse duration, pulse repetition rate, and/or duty cycle. Multiple sequences may be programmed in the device as multiple programmed protocols may be selectable by a user. Protocols delivering predetermined sequences of acoustic energy may be tailored to and, in some embodiments, may generally match, the array of acoustic properties that a tissue exhibiting a particular pathology and/or infection may have. In some embodiments, each acoustic energy delivery sequence, or each programmed protocol may target a specific effect, tissue type, administered agent, or the like.

In yet another aspect, methods and systems of the present invention provide delivery of an irrigating liquid and/or generally high frequency acoustic energy (e.g., ultrasound energy) to a desired internal site of a subject using a catheter assembly. In these embodiments, irrigating fluid and/or acoustic energy is provided to a tissue site, or an obstruction, at an internal target site, such as a site in the vascular system, the respiratory system, the gastrointestinal system, the reproductive system, or the like, using an acoustic energy delivery system for delivery of acoustic energy and tubular structures for delivery of an irrigating liquid. Various systems and methods for delivery acoustic energy to internal body sites for purposes of treatment, disruption, ablation and/or removal of undesired tissue or obstructions, and the like, are known in the art and may be used in systems and methods of the present invention. Various types of catheters employing ultrasound transducers are disclosed, for example, in U.S. Pat. Nos. 5,362,309, 5,318,014, 5,315,998, 5,269,291, 5,197,946, 5,735,811, 5,197,946, 5,989,208, 6,001,069, 6,024,718, 6,623,444, 6,855,123 and 7,297,131, the disclosures of which are incorporated herein by reference in their entireties.

In some embodiments, delivery of an irrigating liquid and/or acoustic energy at particular frequencies, intensities, pulse durations, pulse repetition rates, and/or duty cycles using a catheter-based system, may be selected to promote effects such as immune modulation, improved vascularization, bioacoustic effects and efficacy of administered agents such as antibiotic, anti-restonosis and other agents. Delivery of one or more sequences of acoustic energy, with each sequence providing delivery of acoustic energy at a different frequency, intensity, pulse duration, pulse repetition rate, and/or duty cycle may be provided and multiple sequences may be programmed in a catheter-based system as multiple programmed protocols selectable by a user.

Fluid and/or aerosol particles and/or droplets may be supplied in addition to delivery of high frequency acoustic energy through acoustic energy delivery systems of the present invention, in a continuous or pulsed delivery protocol, to tissue surfaces or to obstructions to promote penetration of blocked sites such as nasal passages, disruption and opening of undesired blockages, and/or to provide cooling of the target site during or following delivery of high frequency (e.g., ultrasound) acoustic energy. Pulsed delivery using high frequency pulsations promotes entry (e.g., by the Helmholtz principle), biofilm dissolution and acoustic enhancement of medications delivered in the liquid stream and/or aerosol droplets.

Devices of the present invention may incorporate one or more aspiration ports for removal of materials from a working site prior to, during or following delivery of fluid and/or aerosol particles/droplets and/or generally high frequency acoustic energy. Multiple delivery ports may be provided for delivery of multiple (different) fluids, or for delivery of multiple types of aerosol particles/droplets, sequentially or simultaneously. Visualization and/or illumination of intranasal target sites may be provided using optical, acoustic, or other types of visualization and illumination systems incorporated in devices of the present invention. An endoscopic port may be provided for delivery of diagnostic and/or therapeutic tools, agents, and the like. Systems for delivering additional diagnostic and/or treatment modalities such as electromagnetic radiation, radio frequency radiation, laser radiation, microwave radiation, and the like, may also be provided in connection with methods and systems of the present invention. In one embodiment, systems of the present invention may additionally be adapted for delivery and placement of implantable devices, such as stents.

Devices of the present invention may also incorporate one or more systems, such as one or more discrete receptacle(s), for collection of material removed by aspiration. The collected tissue, obstruction and/or debris samples may be subjected to various types of diagnostic testing, characterization, and the like. Multiple collection receptacles may be provided for collection of samples at different stages of a protocol.

BRIEF DESCRIPTION OF THE DRAWINGS

FIGS. 5A-5C show schematic drawings illustrating a device similar to that shown in FIG. 3 for placement and expansion of an expandable member (e.g., balloon) in a body cavity and shows, schematically in cross-section, the internal anatomy of the nasal passageways. FIG. 5A shows an expandable member partially expanded in a nasal and/or sinus cavity; FIG. 5B shows the expandable member nearly fully deployed to contact the internal surface of a nasal/sinus cavity; and FIG. 5C schematically shows the application of energy, such as acoustic energy, through fluid in the expandable member and delivery of that energy to surrounding tissues.

FIG. 7 shows a schematic drawing of another device of the present invention for delivering acoustic energy (e.g., sonic acoustic energy as well as ultrasound energy) to a tissue surface, with or without delivery of fluid and/or aerosol particles or droplets.

FIG. 8B showing extension of an active therapeutic component for delivering generally high frequency acoustic energy (e.g., ultrasound energy) to a blockage in the osteomeatal complex in the nasal/sinus passageway; FIG. 8C schematically showing delivery of acoustic energy through the active therapeutic component to disrupt the blockage in the osteomeatal complex; and FIG. 8D showing aspiration of debris from the site, and FIG. 8E showing the internal passageways and cavities cleared of debris.

FIG. 8F shows insertion of the device and initial deployment of the stent over a guide; FIG. 8G shows further deployment of the stent along the guide in the osteomeatal complex; and FIG. 8H shows final positioning of the stent in the osteomeatal complex.

FIG. 9A shows insertion of the device and initial deployment of the expandable member over the proximal portion of the guide; FIG. 9B shows further deployment of the expandable member along the guide; FIG. 9C illustrates one embodiment of an expandable member fully deployed over a guide to intimately contact internal passageways and cavities; and FIG. 9D schematically shows the application of energy, such as acoustic energy, through fluid contained in the expandable member and delivery of that energy to surrounding tissues.

FIG. 10A shows a schematic diagram illustrating a control device, a catheter and an enlarged view of a distal operating head having properties similar to the device shown in FIG. 3; FIG. 10B shows a schematic diagram illustrating a control device, a catheter and an enlarged view of a distal operating head having properties similar to the device shown in FIGS. 5A-5C; and FIG. 10C shows a schematic diagram illustrating a control device, a catheter and an enlarged view of a distal operating head having properties similar to the device shown in FIGS. 7, 8A-8D, 8F-8H and 9A-9D.

Like numbers have been used to designate like parts throughout the several drawings to provide a clear understanding of the relationship of the various components and features, even though different views are shown. It will be understood that the appended drawings are not necessarily to scale, and that they present a simplified, schematic view of many aspects of systems and components of the present invention. Specific design features, including dimensions, orientations, locations and configurations of various illustrated components may be modified, for example, for use in various intended applications and environments.

DETAILED DESCRIPTION

Specific methods and systems of the present invention for pulsed delivery of liquids and/or aerosols, and/or for delivery of generally high frequency, generally high intensity acoustic energy (e.g., ultrasound) to intranasal areas such as nasal passages, sinuses and sinus ostia, are described with reference to the accompanying drawings. It will be appreciated that these specific embodiments are illustrative, and that systems and methods of the present invention may be used in a variety of applications, as described elsewhere in this specification.

Figure 1:
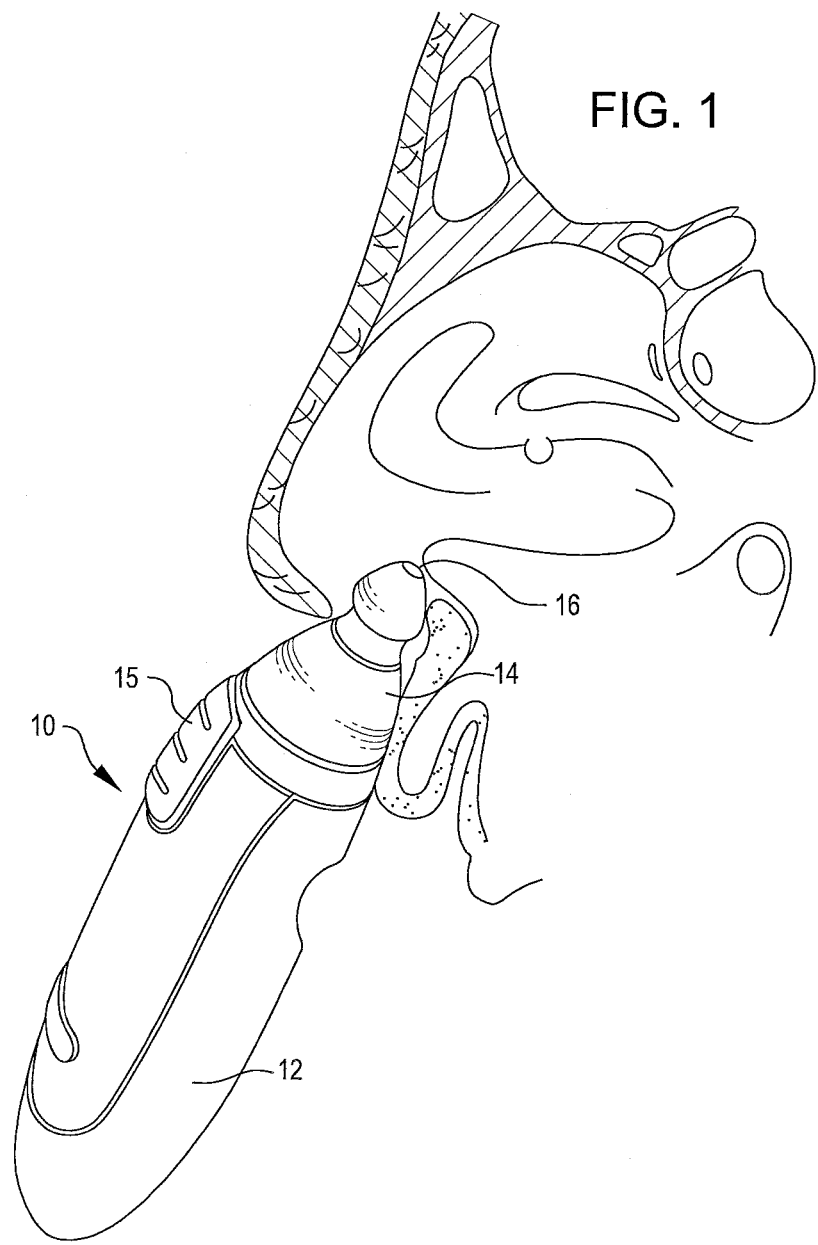
FIG. 1 shows a schematic illustration showing a handheld device of the present invention for delivering fluid and/or aerosol particles or droplets to a tissue surface or an obstruction, the device being shown inserted into a user's nostril and the illustration showing, in cross-section, the internal anatomy of the nasal passageways.

FIG. 1 shows a schematic illustration of one embodiment of device for pulsed delivery of liquids and/or aerosols to a subject's nasal passages. As shown in FIG. 1, device 10 comprises a handle 12, a nostril interface member 14 and a discharge port 16. Handle 12 has a size and configuration that facilitates holding in one or both hands and may include ridges, indentations, curved contours, and the like, to enhance the ergonomic feel and secure handling of the device. Handle 12 may include at least one activation mechanism, such as control 15, for activating one or more device functions. In one embodiment, for example, control 15 may be operated by a user to activate, or inactivate, a pulsatile flow of liquid and/or aerosol from discharge port 16 in nostril interface member 14.

Handle 12 may also house power supply and control elements for operating the device. Power may be supplied to device 10 by physical connection to an electrical power source such as a separate control unit or an electrical outlet by means of a conventional power cord, as is well known in the art. Power may alternatively be supplied by a battery source mounted in the handle. Battery power sources may be provided as replaceable or rechargeable components. Battery charging may be accomplished by direct coupling of battery terminals, or conductive elements provided on the housing, with a power source, or by indirect coupling using, for example, an inductive charging system. Handle 12 may also house control mechanisms, such as mechanical or electronic switches, microprocessors, power supplies, and the like, and may house an aerosol generation device and/or the system for generating pulsatile discharge of liquid and or aerosol droplets.

Handle 12 and nostril interface member 14 may be provided in an integrated, single piece construction, or they may be provided as separate components that are detachable from one another. Nostril interface member 14 comprises at least one discharge port 16 at a distal end of the member, and generally has a size and configuration that permits insertion of a distal end of the interface member and discharge port 16 into the nostril of a user. The distal end of the nostril interface member may have a generally curved or tapered configuration, with a smaller diameter area at the discharge outlet, such that the discharge outlet and distal end of the interface member may be inserted into the nostril, while more proximal surfaces of the nostril interface member contact the nostril opening and effectively "seal" the opening during use of the device. In some embodiments, the nostril interface member may be flexible and may comprise a telescoping structure that permits extension and retraction of the member, or adjustment of the member to different sizes or configurations. In some embodiments, the nostril interface member may be articulatable with respect to the handle.

In one embodiment, devices of the present invention are capable of delivering a liquid stream in a generally high frequency pulsatile flow. In another embodiment, devices of the present invention are capable of generating aerosol particles and/or droplets, and delivering the aerosol particles and/or droplets in a generally high frequency pulsatile flow. In yet another embodiment, devices of the present invention are capable of selectively delivering a liquid stream, aerosol particles and/or aerosol droplets, simultaneously or sequentially, in a generally high frequency pulsatile flow. Liquid, aerosol particles and/or aerosol droplets may be delivered from a common discharge port sequentially and intermittently, or from multiple, dedicated discharge ports, simultaneously or sequentially, and on a continuous or intermittent basis.

An aspiration channel may optionally be provided for removal of material loosened by the application of pulsed liquid and/or aerosol flows from a site, such as nasal passageways. Aspiration may be provided through a common port as fluid and/or aerosol delivery, or through an additional aspiration port provided in the nostril interface member 14, or through an aspiration port provided in an auxiliary device. Although an aspiration system employing a vacuum device may be provided integrally with the device and an aspiration reservoir may be incorporated into the device or used in connection with the device, aspiration may also be accomplished by interfacing an aspiration channel within the device with a vacuum or suction source provided in a medical facility. Interface tubing may be provided for this purpose.

Figure 2A:
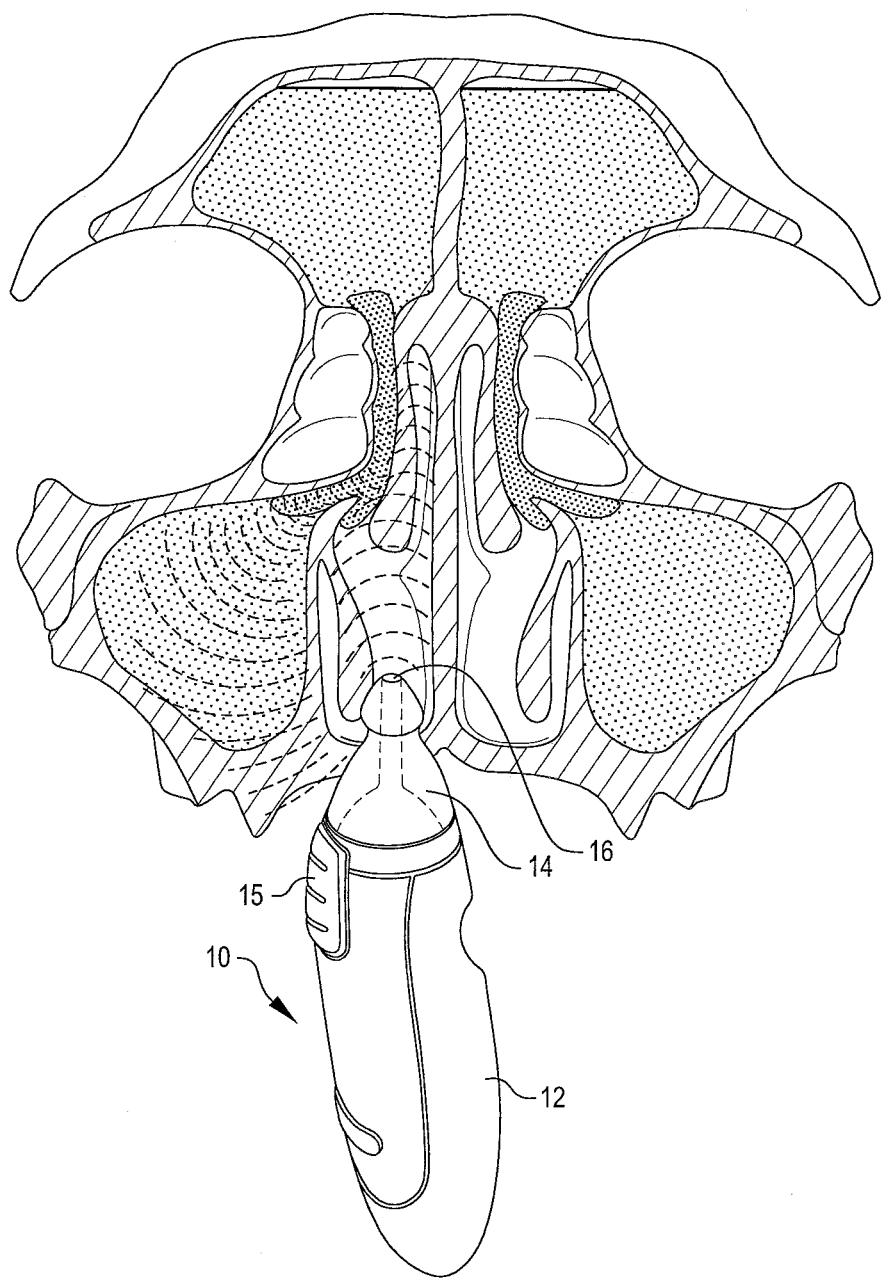
FIGS. 2A and 2B show schematic diagrams illustrating the use of a device shown in FIG. 1, with FIG. 2A showing insertion of the device into a nostril and operation of the device to distribute an irrigating fluid and/or aerosol pulsed at high frequency in the area of clogged nasal passageways, and FIG. 2B showing subsequent aspiration of the material from the passageways as a result of delivery of the irrigating fluid and/or aerosol.
Figure 2B:
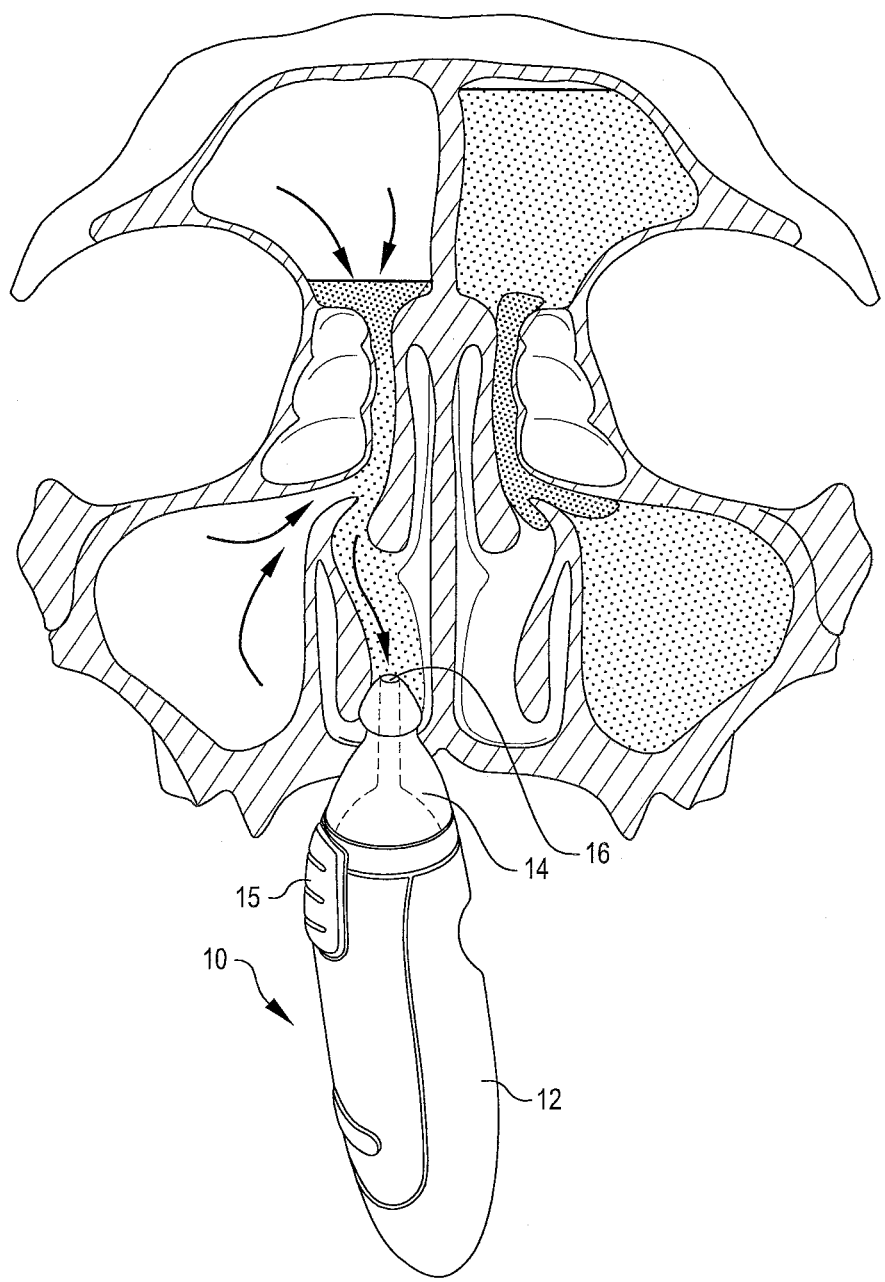

FIGS. 2A and 2B show, schematically, operation of a device as illustrated in FIG. 1. Nostril interface member 14 is inserted into and generally contacted to a user's nostril. For some applications, the nostril interface member may be sized and configured to form a substantially liquid-tight seal against a user's nostril when inserted and upon continued application of pressure in the insertion direction. After insertion and placement of the nostril interface member, the user activates a desired delivery protocol for delivery of a liquid stream, aerosol particles and/or aerosol droplets, simultaneously or sequentially, in a generally high frequency pulsatile flow, through discharge port 16. This is shown schematically by the curved dashed lines. The pulsatile delivery of liquids and/or aerosols facilitates penetration of fluids and particles through passageways and blockages and may also deliver a therapeutic effect to tissue surfaces. Liquids and other material, including debris, mucus, infected tissue, and the like may be withdrawn by aspiration using the same device following pulsatile delivery of liquids and/or aerosols, as shown schematically in FIG. 2B.

Controls may be provided on the device handle, illustrated as actuator 15, or on an accessory device or module, allowing a user to select liquid and/or aerosol delivery modes, or allowing a user to select among various modes of operation or various pre-determined operating programs. In one embodiment, for example, a device such as that illustrated in FIG. 1 may be operated in an aerosol delivery mode whereby, upon activation, aerosol particles and/or droplets are pulsated and discharged from outlet port 16 at a generally low pressure and high frequency. In another embodiment, a single mode device may be operated in a liquid delivery mode whereby, upon activation, a high frequency pulsating liquid stream is discharged from outlet port 16, continuously or intermittently. In yet another embodiment, a user may select pulsating liquid and/or aerosol discharge modes which may also operate on a continuous or intermittent basis.

In some embodiments, multiple pulsating irrigation fluid and/or aerosol delivery options may be programmed in the device, with various operating programs being predetermined and, optionally, selectable by the user. In one embodiment, for example, a control may be actuated by a user to initiate a predetermined or selectable cycle involving multiple irrigation fluid and/or aerosol delivery protocols. Multiple different delivery protocols may involve delivery of irrigation fluid and/or aerosol at pulsation rates having a selected frequency, intensity, pulse duration, pulse repetition rate, duty cycle, and the like. Multiple different delivery protocols may additionally involve delivery of different types (e.g., composition, concentration, osmolarity, and the like) of irrigation fluids, and/or different types (e.g., composition, concentration, particle size, and the like) of aerosols.

In one embodiment, for example, a therapeutic cycle may provide delivery of from one to several different pulsation cycles that correlate with the acoustic properties of each contributing pathologic process that contributes to the disease or symptomology (e.g., sinusitis, ear infection, pneumonia, chronic skin wounds, gastroenterologic processes, tumors, and the like.) Pathologic processes that may be targeted by the therapeutic cycle may include (but are not limited to) biofilms, inflammation, mechanical obstruction, hypertrophy, poor circulation, lithiases (stones/calcifications), dysfunctional immune response/modulation, and the like. In alternative embodiments, a user may select pulsating liquid rinse and/or aerosol delivery options by means of multiple selectable actuators. In any of these embodiments, multiple and selectable modes may be implemented, whereby programmed or selectable levels of liquid and/or aerosol flow or volume, aerosol particle and/or droplet size, aerosol particle and/or droplet density, pulsation frequency, temperature, and the like, may be selectable by the user.

In one embodiment, for example, different pulsation characteristics may be provided to promote different effects. Optimal pulsation frequencies for promoting sinus entry (resonance), biofilm dissolution, drug enhancement, immunomodulation and circulatory regulation may be different; user selectable controls may be provided for selecting pulsation frequencies or modes of operation to promote each of these functions. Alternatively, one or more pre-programmed timing sequences of application of multiple frequencies may be provided.

Aerosol generation may be accomplished using aerosol generators, such as pumps, aperture plates or diaphragms, ultrasound transducers (e.g., piezoelectric crystals), and other systems that are well known in the art. In one embodiment, solution provided at a generally low pressure is conveyed through a standard jet nebulizer to produce aerosol or finely divided liquid droplets. Aerosol droplets generated and discharged by devices of the present invention preferably have a droplet size of from about 0.5μ to about 200μ, in some embodiments from about 1μ to about 100μ, in other embodiments from about 3μ to about 60μ, and in yet other embodiments from about 5μ to about 30μ, entrained in gas (e.g. air).

Pulsation of the liquid and/or aerosol particles and/or droplets is generally accomplished at a frequency in excess of 100 Hz and may be accomplished at an ultrasound frequency of 20 kHz or higher. Devices of the present invention may provide either or both ultrasonic and sub-ultrasonic (sonic) oscillation of a liquid stream or aerosol as it exits the discharge outlet. A liquid flow may be pulsated at one frequency, such as a frequency less than 10 kHz, while aerosol droplets may be pulsated at a different frequency, generally at a higher frequency. Aerosol may be pulsated at frequencies in excess of about 1500 Hz, and in some embodiments in excess of about 5000 Hz, and generally at frequencies less than 10 MHz. In some embodiments, aerosol is pulsated at frequencies in excess of about 10 kHz, from about 10 kHz to about 100 kHz, in some embodiments from about 15 kHz to about 50 kHz, and in yet other embodiments from about 20 kHz to about 40 kHz.

Aerosol particles or droplets may alternatively be pulsated at two or more alternating frequencies. In one embodiment, aerosol may be pulsated at multiple alternating, sub-ultrasonic frequencies. In another embodiment, aerosol is pulsated at two or more alternating frequencies, with one or both of the frequencies being an ultrasonic frequency. According to one embodiment, for example, aerosol delivery is provided by pulsation at multiple frequencies, such as at an ultrasonic frequency of from about 20 kHz to about 40 MHz and at one or more additional ultrasonic or sub-ultrasonic frequencies.

The pulsation frequency of delivery of liquid and/or aerosol streams may be alternated by providing multiple pulsation generators, or by operating a single pulsation generator at different frequencies and/or energies. Various cycles may be implemented and, in some embodiments, a user may selectively control aerosol generation and pulsation, while in other embodiments, predetermined cycles of aerosol generation and pulsation may be provided. In one embodiment, for example, a column of mist is generated in the space between the transducer and an aerosol discharge orifice when the transducer is operated at the aerosol generation frequency, and the column of mist is then pulsated as it exits the discharge orifice when the device is operated at the pulsation frequency. Cycles may be established, and predetermined, to operate the transducer in an aerosol generation mode for a time sufficient to generate a suitable aerosol column, and then to operate the transducer in the pulsation mode for a time sufficient to discharge the aerosol from the column.

According to some embodiments, a single piezoelectric crystal or another ultrasound generating device may be operated in different modes, sequentially, to produce both aerosol and high frequency pulsations of liquid and/or aerosol. In another embodiment, multiple ultrasound transducers (e.g., two piezoelectric crystals) may be operated in aerosol generation and pulsation modes, respectively, simultaneously or intermittently, to generate aerosol and then to pulsate the generated aerosol at a generally high frequency. A dedicated aerosol generation transducer may be operable, for example, in a single operating condition or in multiple operating conditions, and a dedicated pulsation transducer may, similarly, be operable at a single pulsation frequency, or at multiple selectable pulsation frequencies.

In one embodiment, an aerosol generation system (e.g., a piezoelectric crystal or ultrasound transducer) and an aerosol pulsation system (e.g., an ultrasound transducer) are located separately. An aerosol generation transducer may be located at a liquid solution interface, for example, to generate a column of aerosol droplets extending above the liquid solution interface. An aerosol pulsation system, such as an ultrasound transducer, may be located along an aerosol column or in proximity to an aerosol discharge orifice, providing pulsatile discharge of aerosol from a discharge port.

In another embodiment wherein ultrasound transducers are used both for aerosol generation and pulsation, an aerosol generation transducer and an aerosol pulsation transducer may be located in proximity to one another. Multiple transducers may be collocated, for example, with an aerosol generation transducer provided in a central position, and a pulsation transducer provided as an annular transducer positioned around the central aerosol generation transducer to provide pulsation of the aerosol at discharge. Multiple transducers may be operated simultaneously to both generate and pulsate aerosol simultaneously. Alternately, an aerosol generator may be operated to generate a column of aerosol and the aerosol pulsation transducer may be operated independently to pulsate to the generated aerosol. The aerosol generation transducer may be immersed in liquid and in direct contact with the liquid, or it may be in indirect contact with liquid through a flexible membrane or diaphragm.

Devices of the present invention may additionally incorporate a heater, or a thermostat for controlling the temperature of liquid discharged in a liquid stream, of for controlling the temperature aerosol at or prior to discharge. A heating element may be provided, for example, in proximity to a wall defining the mist column to heat the mist as it moves through the column to a temperature of from about 30-50° C., in some embodiments from about 35-45° C., and in yet other embodiments from about 38-43° C. In some embodiments, the aerosol is heated to a temperature above the average human body temperature (37° C.) prior to discharge from the device.

Figure 3:
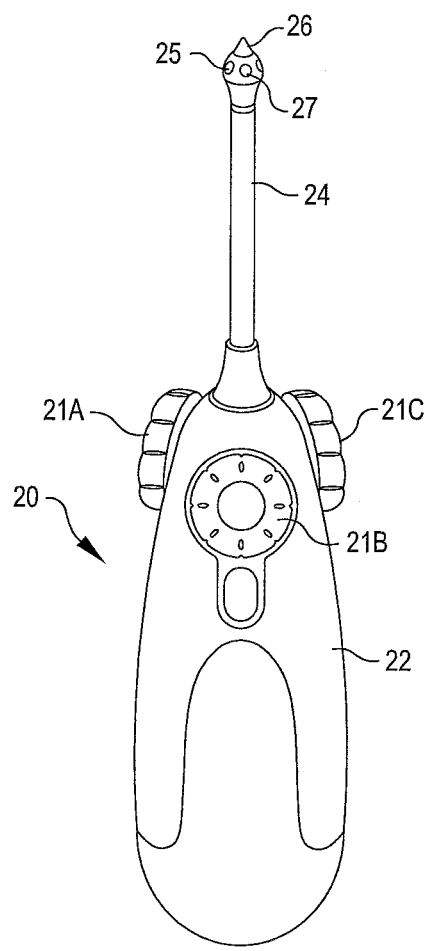
FIG. 3 shows a schematic drawing illustrating another embodiment of a device of the present invention for delivering fluid and/or aerosol particles or droplets and/or acoustic energy (e.g., sonic acoustic energy as well as ultrasound energy) directly to a tissue surface.
Figure 4:
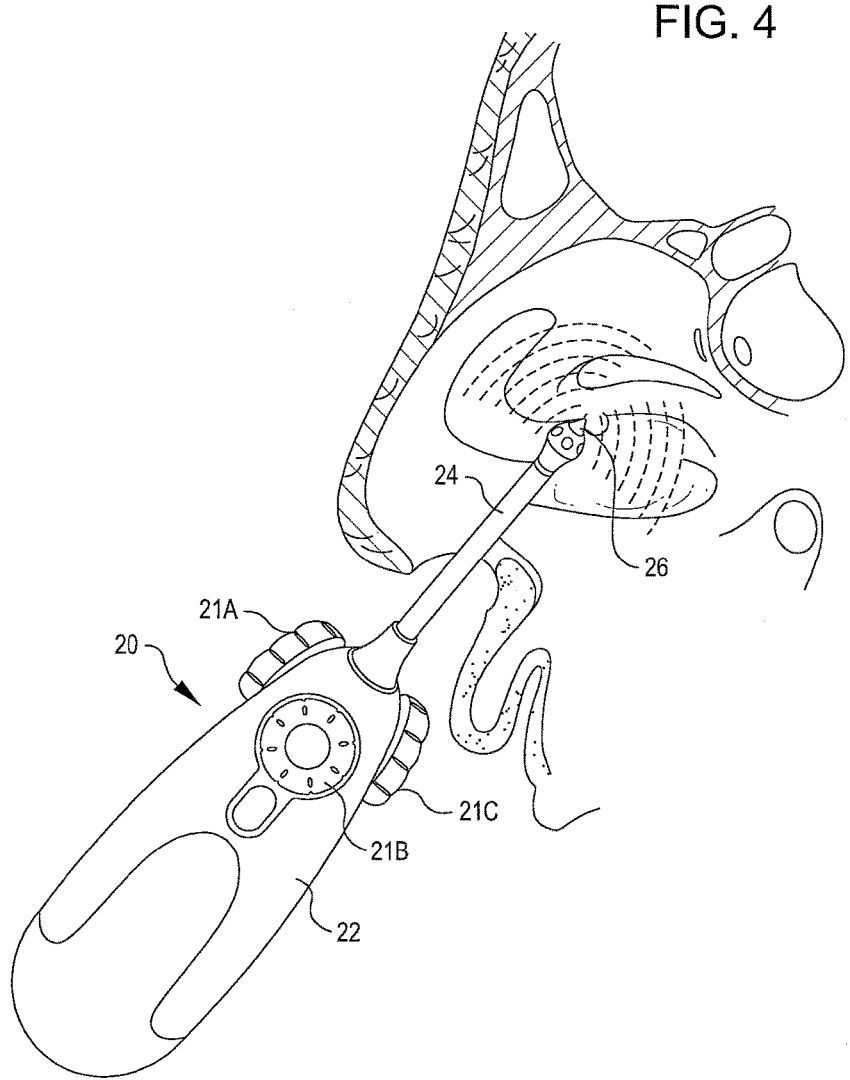
FIG. 4 shows a schematic drawing illustrating the device of FIG. 3 inserted into a user's nasal passageway to deliver fluid and/or aerosol particles or droplets and/or acoustic energy (e.g., sonic acoustic energy as well as ultrasound energy) directly to a tissue surface in the nasal passageway and shows, schematically in cross-section, the internal anatomy of the nasal passageways.

FIGS. 3-5 show schematic illustrations of devices of the present invention for delivery of generally high frequency acoustic energy (e.g., sonic and/or ultrasound energy, including high intensity ultrasound (HIU) and high intensity focused ultrasound (HIFU)) to tissue sites such as nasal passages. As shown in FIG. 3, device 20 comprises a handle 22, an insertion wand 24 and an acoustic energy delivery member 26. In devices intended for delivery of high frequency (sonic and ultrasound) acoustic energy directly to internal sites, such as nasal and sinus passageways, insertion wand 24 is configured for insertion through a nostril opening and positioning at least partially within nasal passageways. Insertion wand 24 is generally cylindrical and may be constructed as a flexible, catheter-like structure having at least one longitudinally oriented lumen extending therethrough. External surfaces of the insertion wand may be provided with a surface texture, or coating, such as a hydrophilic or hydrophobic coating, to ease passage of the insertion wand though nasal passages and improve deliverability. External surfaces of the insertion wand may also be provided with antibacterial coatings or coatings through which drugs or other agents are provided.

Insertion wand 24 may incorporate multiple lumens, channels or the like that communicate with source liquids, aerosol particles and/or droplets, vacuum sources, liquid and/or vacuum manifolds, or the like, to provide delivery of liquids, aerosol particles and/or droplets, vacuum, or the like, to intranasal passages. Multiple lumens may be co-axial with respect to one another, or they may be aligned on different axes and be non-concentric with respect to one another. In these embodiments, insertion wand 24 is generally provided with one or more discharge ports 25 in proximity to a distal area, providing intranasal delivery of a liquid and/or aerosol particles and/or droplets. Insertion wand 24 may, alternatively or additionally, be provided with one or more aspiration ports 27 in proximity to a distal area, providing withdrawal of delivered liquids and degraded materials from an intranasal site when an aspiration system (e.g. vacuum) is activated. A distal end of insertion wand 24 may additionally incorporate an endoscopic port and/or components of a visualization system, such as an optical or ultrasound guidance and/or visualization system.

Energy delivery member 26 may be provided at the tip of the insertion wand and configured for positioning in proximity to and/or contacting blockages within nasal passages, mucous membranes and nasal turbinates, or pathological or undesired tissue. In one embodiment, energy delivery member 26 may comprise a tapered structure, such as a generally conical structure, for focusing and concentrating high frequency and/or high intensity acoustic energy. Conical structures for delivering high intensity focused ultrasound are described, for example, in U.S. Pat. Nos. 6,666,835, 6,500,133 and 6,217,530. An energy delivery member or surface may be extendible and/or retractable with respect to handle 22 and/or insertion wand 24 to provide desired positioning of the energy delivery member in contact with obstructions and/or tissues for delivery of high frequency acoustic energy. In some embodiments, the energy delivery member, and/or distal portions of the insertion wand, may be constructed of a light transmitting material, and the device may be adapted to delivery light energy, such as but not limited to ultraviolet light energy, to a desired through the energy delivery member and/or the insertion wand.

Figure 5B:
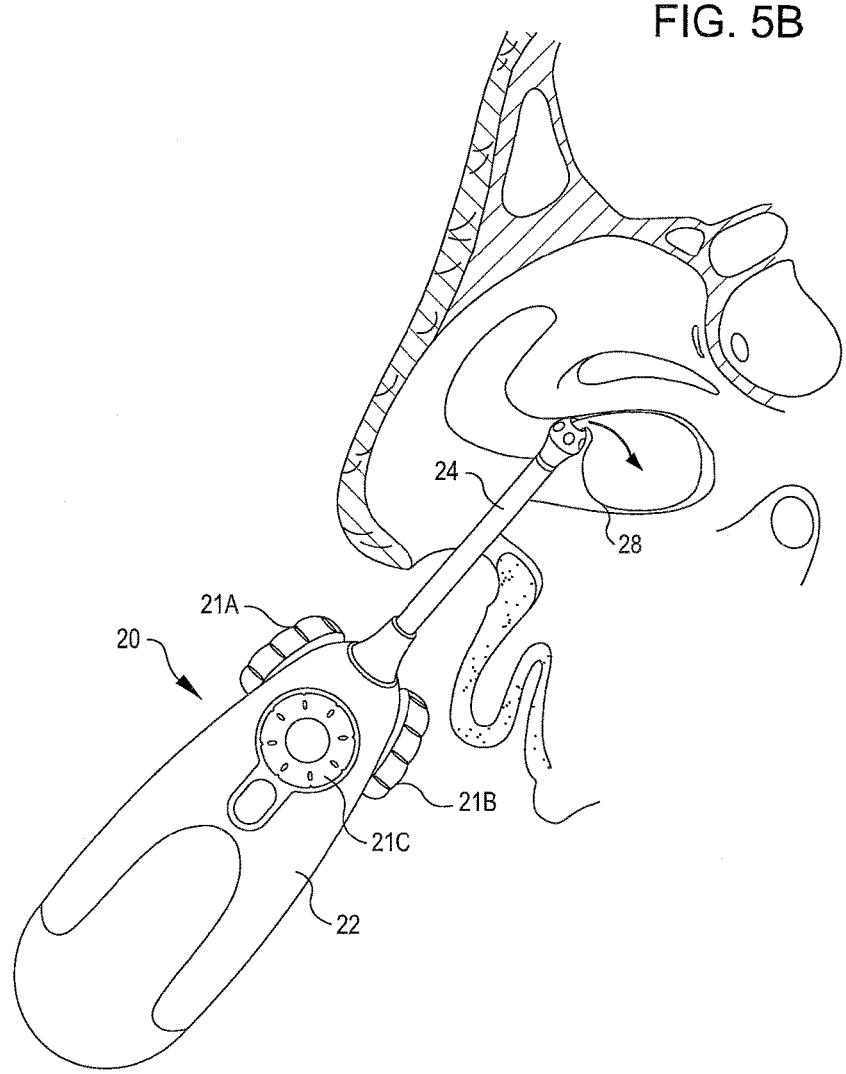
Figure 5C:
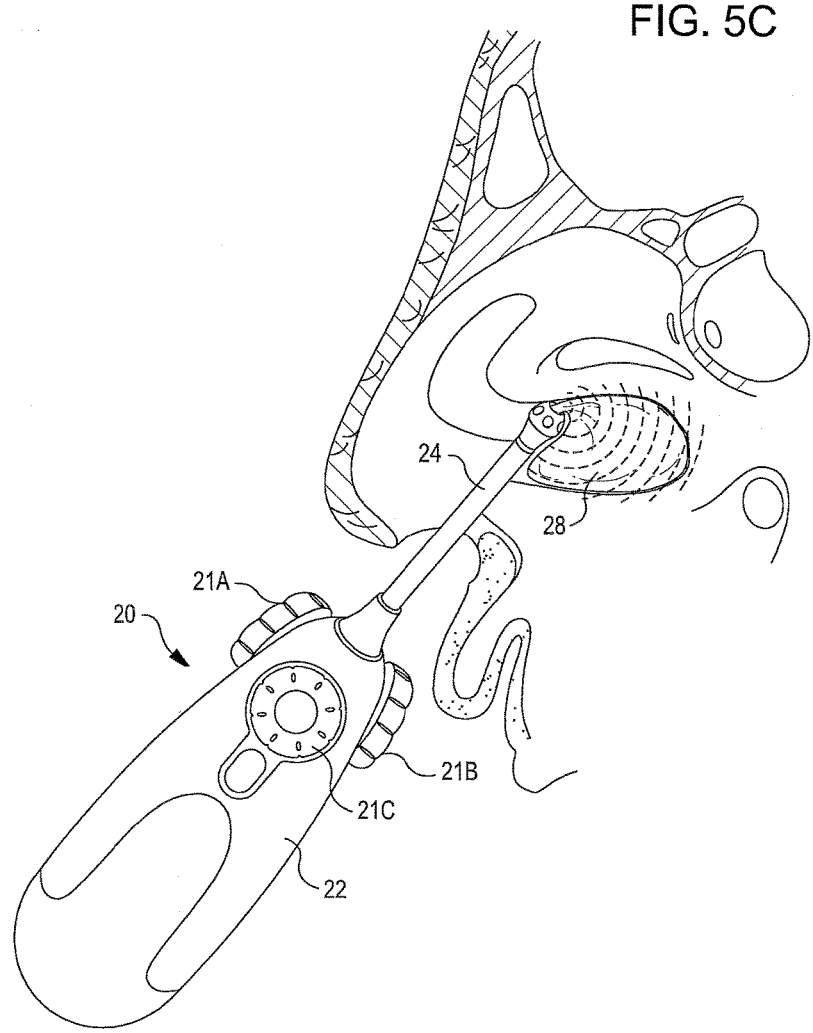

In another embodiment, as illustrated in FIGS. 5A-5C, an energy delivery member may comprise a flexible, deformable bladder or inflatable chamber 28 adapted for retaining an acoustically transmissive material, such as a liquid or gel, within its interior volume. The chamber is controllably expandable to contact tissue surfaces in oddly shaped and unevenly contoured cavities, providing delivery of acoustic energy, through the acoustically transmissive material contained within the interior volume, to tissue surfaces contacting and in close proximity to the chamber. Delivery of acoustic energy, such as ultrasound energy, to tissues forming the walls of cavity and passageway lumens is otherwise difficult.

The flexible, deformable chamber may be stored in a collapsed condition within wand 24, for example, and expanded, or inflated, at the desired target site from a distal tip of the wand by filling with an acoustically transmissive material. Expandable chamber 28 may be enlarged at a desired target site, as shown schematically in FIGS. 5A-5C, until the walls of the chamber contact a tissue site, such as the walls of a cavity or passageway or lumen. The chamber walls may be expanded to contact, or be positioned in close proximity to, walls of irregularly shaped cavities and passageways for delivery of energy to the tissue. Energy, such as generally high frequency acoustic energy, e.g. ultrasound energy, may be applied to the tissue surfaces or obstructions in contact with the chamber wall by transmission of the acoustic energy through the acoustically transmissive material and the wall of the inflatable chamber to deliver acoustic energy directly to the tissue contacting or in close proximity to the wall of chamber wall, and to neighboring tissues as shown schematically in FIG. 5C. This embodiment provides effective delivery of ultrasound energy to tissue surfaces, cavities and obstructions over a larger surface area than point contact and provides effective access to target sites that may otherwise be difficult to access with an ultrasound applicator.

The bladder or inflatable member(s) may be constructed from a material that has generally high acoustic transmissivity properties and that, when filled with an acoustically transmissive material, provides a flexible surface that is expandable and deformable to conform to contours of internal cavities or passageways, such as intranasal passages. The inflatable member may be coated with a drug or another agent, particularly an agent whose activity is enhanced in the presence of high frequency acoustic energy, such as ultrasound energy.

An expandable chamber may also be employed for delivery of a composition such as a drug or another agent, to internal body cavities and passageways. The inflatable member may, for example, be permeable or porous over at least a portion of its surface to deliver a drug or another agent to a target site. In one embodiment in which the system is used to delivery high frequency acoustic energy to a desired target site, the inflatable member may be expanded using a substance comprising both an acoustically transmissive material and one or more bioactive compositions. The bioactive composition(s) may be eluted or otherwise released from the expandable member prior to or during delivery of acoustic energy through the expandable member. This embodiment may be employed, for example, for delivery of an agent whose activity is enhanced in the present of high frequency acoustic energy, such as ultrasound, to the target site.

A distal end of the energy delivery member is preferably navigable to desired treatment sites, such as tissue surfaces and obstructions, such as blocked sites within nasal passages, where it can be activated to provide mechanical and cavitational effects that promote recanalization of obstructed passages. The energy delivery member may have a pre-formed shape or it may be flexible or conformable, as described above. Energy delivery members having different pre-formed shapes may also be used. A proximal end of energy delivery member 26 is connected or connectable to a generally high frequency acoustic energy generator (e.g., an ultrasound transducer) or acoustic energy coupling, providing delivery of high frequency acoustic energy (e.g., ultrasound) to the energy delivery member.

High frequency acoustic energy delivered through energy delivery member 26, or through an energy delivery member incorporating an expandable chamber, generally has a frequency of greater than about 20 kHz and less than about 25 MHz; in some embodiments from about 20 kHz to about 100 kHz; in some embodiments from about 20 kHz to about 50 kHz; in other embodiments greater than about 100 kHz and less than about 1 MHz; in other embodiments from about 500 kHz to about 15 MHz; and in yet other embodiments greater than about 500 kHz and less than about 5 MHz. The acoustic energy applied through the energy delivery member may be at a generally high intensity of from about 1 mW/cm$^2$ to about 5 W/cm$^2$; in some embodiments from about 50 mW/cm$^2$ to about 3 W/cm$^2$; in other embodiments from about 5-100 mW/cm$^2$; in yet other embodiments from about 0.1-1.5 W/cm$^2$. In other embodiments, the acoustic energy applied through the energy delivery member may be a generally high intensity ultrasound of greater than about 1 W/cm$^2$ and less than about 25 kW/cm$^2$. In some embodiments, the acoustic energy applied through energy delivery member has an acoustic intensity from about 10 to about 1,000 W/cm$^2$; in some embodiments from about 1,000 to about 15,000 W/cm$^2$; and in yet other embodiments from about 3,000 to about 10,000 W/cm$^2$. The generally high intensity ultrasound may be sufficient to ablate tissue and/or cellular structures or debris, or it may be at a sub-ablation intensity that is sufficient to disrupt tissue and/or cellular structures or debris but not ablate. The pulse duration and repetition rate may be adjusted and matched to the frequency and intensity of acoustic energy pulses to achieve the desired effect.

The high frequency acoustic energy may be selectably activated on a continuous basis, or ultrasound energy may be applied, through the energy delivery member, on an intermittent basis, and the frequency and/or acoustic intensity may be adjustable and selectable by the operator. Operation of the ultrasound transducer at duty cycles of less than about 80% is generally preferred; in some embodiments at duty cycles of less than 50%; and in yet other embodiments at duty cycles of less than about 30%. Enhancement and/or coupling agents promoting and/or targeting acoustic energy deposition may be used and may be provided to a target site through the insertion wand and/or the energy delivery member.

Handle 22 has a size and configuration that facilitates holding in one or both hands and may include ridges, indentations, curved contours, and the like, to enhance the ergonomic feel and secure handling of the device. Handle 22 may house power supply and control elements for operating the device. Power may be supplied to device 20 by physical connection to an electrical power source such as a separate control unit or an to electrical outlet by means of a conventional power cord, as is well known in the art. Power may alternatively be supplied by a battery source mounted in the handle. Battery sources may be replaceable or rechargeable. Battery charging may be accomplished by direct coupling of battery terminals, or conductive elements provided on the housing, with a power source, or by indirect coupling using, for example, an inductive charging system. Handle 22 may also house control mechanisms, such as mechanical knobs 21A, 21B and 21C, or electronic switches, microprocessors, power supplies, and the like. Knobs 21A, 21B and 21C may provide user operable control of irrigation fluid, aerosol delivery, delivery of generally high frequency acoustic energy, selection of multiple modes of operation and/or multiple programmed protocol sequences, aspiration, other operating modalities, and the like.

Liquids and/or aerosols may be delivered through the insertion wand 24 and ports positioned along or generally at a distal end of the insertion wand, similarly to the delivery of liquids and/or aerosols described with reference to the device illustrated in FIGS. 1, 2A and 2B. Aspiration may also be provided in devices such as those illustrated in FIGS. 3-5, that deliver generally high frequency acoustic energy, such as ultrasound energy. Aspiration may be provided through one or more ports positioned along or generally at a distal end of the insertion wand, similarly to the aspiration feature described with reference to the device illustrated in FIGS. 1, 2A and 2B.

Handle 22, insertion wand 24 and energy delivery member 26 may be provided in an integrated, single piece construction, or they may be provided as separate components that are detachable from one another. Handle 22 may be provided as a single- or multiple-use component. Insertion wands and/or energy delivery members may similarly be provided as integrated components or may be provided separately from one another, with appropriate interfaces for operation. Multiple configurations of insertion wands and/or energy delivery members may be provided for operation on common or multiple handles, with appropriate insertion wands and/or energy delivery members being selectable by a user depending on the circumstances of use. Insertion and energy delivery members may be provided as single- or multiple-use components, although they may generally be provided as sterile, disposable components that are mountable on a reusable handle. Device 20 may incorporate all of the components required for operation, or it may interface with a separate console, or control unit (not shown), that provides electrical power, liquid for infusion or aerosol delivery, operating control features, displays, and the like.

In some embodiments, devices of the present invention are capable of selectively delivering high frequency acoustic energy, a liquid stream, aerosol particles and/or aerosol droplets, simultaneously or sequentially, in one or a plurality of delivery modes: continuous flow; intermittent flow; or high frequency pulsatile flow. Liquid, aerosol particles and/or aerosol droplets may be delivered from a common discharge port sequentially and intermittently, or from multiple, dedicated discharge ports, simultaneously or sequentially, and on a continuous or intermittent basis. Aspiration may be provided, additionally or alternatively, through one or more ports in the insertion wand and/or energy delivery member. Insertion wand 24 may be provided with one or more channels, or lumens, for delivery of liquids, aerosol particles, and/or aerosol droplets to a desired intranasal site, and for removal of material from the site by means of aspiration.

Controls may be provided on the device handle, as illustrated, or on an accessory device or module, allowing a user to select acoustic frequency and/or intensity, liquid and/or aerosol delivery modes, aspiration modes, visualization modalities, or the like. Controls may also be provided allowing a user to select from among various modes of operation or various pre-determined or pre-set operating modes. Devices of the present invention may thus be operated, manually or by selectable automated operation, in a single mode or multiple modes.

In one embodiment, for example, a device such as illustrated in FIGS. 3-5 may be operated in a high frequency acoustic energy deposition mode in which the insertion wand and energy delivery member are positioned in a nasal cavity, with the energy delivery member contacting mucus and/or debris forming an obstruction, or tissue desired to be treated. Acoustic energy delivery may be activated at a preset or selectable acoustic energy frequency and/or intensity to heat and/or cavitate and/or ablate mucus and/or debris forming the obstruction. In another embodiment, the energy delivery member may be positioned to contact tissue and activated at preset or selectable acoustic energy frequency and/or intensity levels to heat and/or cavitate and/or ablate selected tissue sites. Delivery of the high frequency and/or high intensity acoustic energy may be accompanied by infusion of liquids and/or aerosol particles or droplets, and/or by aspiration or liquids, wastes, mucus, and the like, from the site of energy deposition.

In some embodiments, multiple pulsating liquid rinse and aerosol delivery options, as well as multiple energy deposition options, may be programmed in the device, with various operating programs being predetermined and selectable by the user. In alternative embodiments, a user may select pulsating liquid rinse, aerosol delivery and/or energy deposition options by means of multiple selectable actuators. In any of these embodiments, multiple and selectable modes may be implemented, whereby programmed or selectable levels of liquid and/or aerosol flow or volume, aerosol particle and/or droplet size, aerosol particle and/or droplet density, pulsation frequency, temperature, acoustic energy frequency, intensity, pulse repetition rate, duty cycle, and the like, may be selectable by the user.

Figure 6:
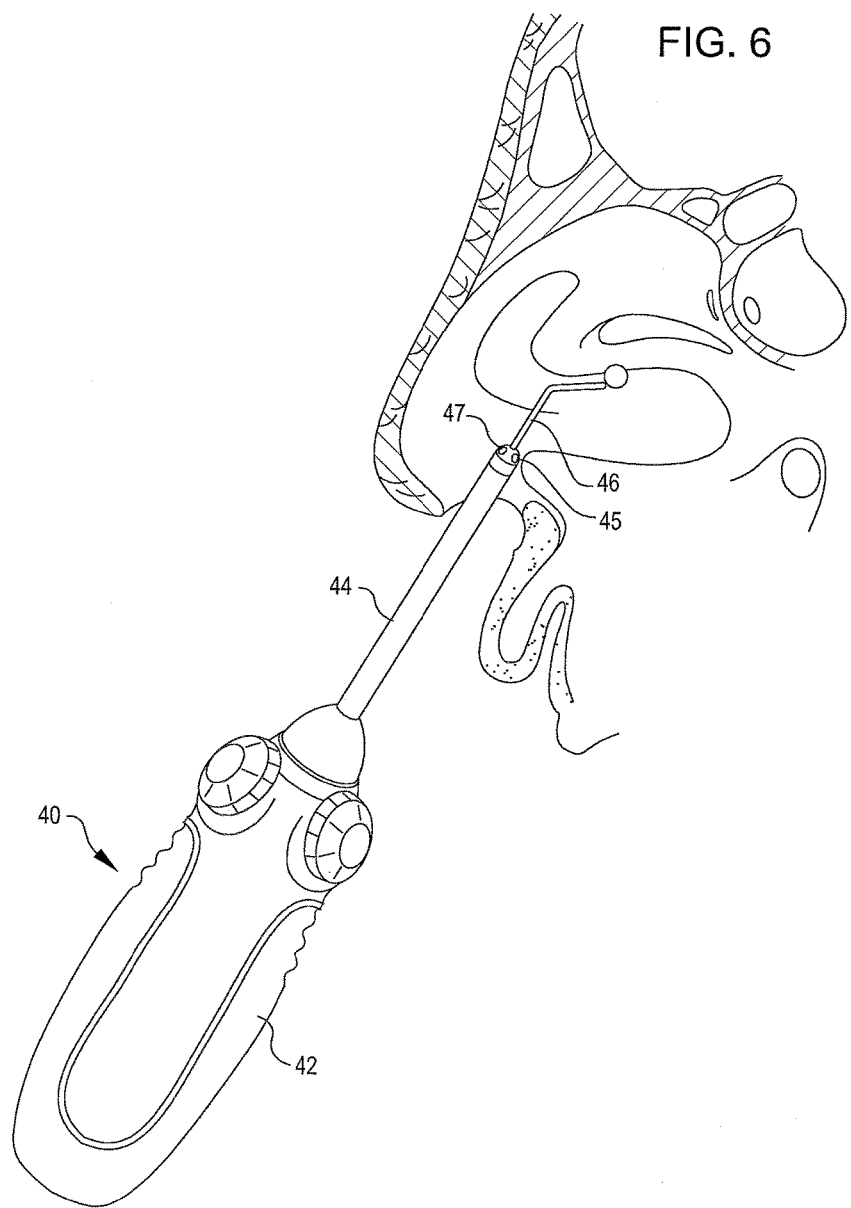
FIG. 6 shows a schematic drawing of another device of the present invention inserted into a user's nasal passageway to deliver acoustic energy (e.g., sonic acoustic energy as well as ultrasound energy) to a tissue surface in proximity to an opening in an ostea in the nasal passageway, with or without delivery of fluid and/or aerosol particles or droplets and shows, schematically in cross-section, the internal anatomy of the nasal passageways.

FIGS. 6 and 7 show schematic illustrations of two embodiments of a device for delivery of generally high frequency acoustic energy to nasal passages. As shown in FIG. 6, device 40 comprises a handle 42, an insertion member 44 and an acoustic energy delivery member 46. Insertion member 44 is configured for insertion through a nostril opening and positioning at least partially within nasal passageways, for example at an opening to an ostea, as shown schematically in FIG. 6. Insertion member 44 is generally cylindrical and may be constructed as a flexible, catheter-like structure having at least one longitudinally oriented lumen extending therethrough. External surfaces of the insertion member may be provided with a surface texture, or coating, such as a hydrophilic or hydrophobic coating, to ease passage of the insertion member though nasal passages and improve deliverability. External surfaces of the insertion member may also be provided with antibacterial coatings or coatings through which drugs or other agents are provided. The coatings may also provide the elution of active compounds from the surfaces during the procedure.

Insertion member 44 may incorporate multiple lumens, channels or the like that communicate with source liquids, aerosol particles and/or droplets, vacuum sources, liquid and/or vacuum manifolds, or the like to provide delivery of liquids, aerosol particles and/or droplets, vacuum, or the like, to intranasal passages. Multiple lumens may be co-axial with respect to one another, or they may be aligned on different axes and be non-concentric with respect to one another. In these embodiments, insertion member 44 is generally provided with one or more discharge ports 45 in proximity to a distal area, providing intranasal delivery of a liquid and/or aerosol particles and/or droplets. Insertion member 44 may, alternatively or additionally, be provided with one or more aspiration ports 47 in proximity to a distal area, providing withdrawal of material from an intranasal site when an aspiration system (e.g. vacuum) is activated. A distal end of insertion member 44 may additionally incorporate components of a visualization system, such as an optical or ultrasound guidance and/or visualization system.

Energy delivery member 46 is generally provided as a structure having a smaller diameter cross-section that that of insertion member 44, providing access to smaller passages or allowing penetration of obstructions. Energy delivery member 46 is configured such that a distal end may be positioned in proximity to and/or contacting tissue surfaces such as mucous membranes and nasal turbinates or polyps, bony protuberances, undesired tissue growths or accumulations or blockages within cavities such as nasal passages. In one embodiment, illustrated in FIG. 6, energy delivery member 46 comprises a generally rigid or semi-rigid wire-like structure capable of conveying, and delivering, high frequency acoustic energy (e.g., ultrasound energy, including high intensity ultrasound (HIU) and high energy focused ultrasound (HIFU)) by contact with tissue or obstructive material along its length and/or at a distal end of the delivery member. In another embodiment, illustrated in FIG. 7, the energy delivery member may comprise a flexible, steerable structure 48. The energy delivery member may be extendible and/or retractable with respect to handle 42 and/or insertion member 44 to provide desired positioning of the energy delivery member in contact with obstructions and/or tissues for delivery of high frequency acoustic energy.

A distal end of the energy delivery member 46, 48 is preferably navigable to target tissue sites or target blocked sites within cavities, such as nasal passages and blocked ostea, where it can be activated to provide mechanical and cavitational effects that promote recanalization of obstructed passages. The energy delivery member 46, 48 may be extendible and retractable with respect to the insertion member 44, as shown in the simplified operational sequence schematically illustrated in FIGS. 8A and 8B. Energy delivery member 46 is generally constructed from an acoustically transmissive material and may have different stiffness properties along its length, providing steerability. The energy delivery member may have a pre-formed shape, illustrated as an angled shape as shown in FIG. 6, or may be flexible or conformable, as illustrated schematically in FIG. 7. Energy delivery members having different pre-formed shapes may also be used. The energy delivery member may be constructed from metallic materials, such as Nitinol. Wire-like energy delivery members may be covered with another acoustically transmissive material, such as a resilient rubber-like material, that may function to delivery high frequency acoustic energy uniformly or in a focused fashion.

A proximal end of energy delivery member 46, 48 is connected or connectable to a generally high frequency acoustic energy generator (e.g., an ultrasound transducer) or acoustic energy coupling, providing delivery of high frequency acoustic energy (e.g., ultrasound) along the length of and to a distal end of the energy delivery member 46, 48. In some embodiments, a guidance member, such as a guide-wire-type member, may be provided and operated separately from an energy delivery member. In this embodiment, the guidance member may be advanced and positioned at a desired operating site, and the energy delivery member may then be advanced over, along-side or through the guidance member for positioning and activation at the desired operating site.

High frequency acoustic energy delivered through energy delivery members 46, 48 generally has a frequency of greater than about 20 kHz and less than about 25 MHz; in some embodiments from about 20 kHz to about 100 kHz; in some embodiments from about 20 kHz to about 50 kHz; in other embodiments greater than about 100 kHz and less than about 1 MHz; in other embodiments from about 500 kHz to about 15 MHz; and in yet other embodiments greater than about 500 kHz and less than about 5 MHz. The acoustic energy applied through the energy delivery member may be at a generally high intensity of from about 1 mW/cm$^2$ to about 5 W/cm$^2$; in some embodiments from about 50 mW/cm$^2$ to about 3 W/cm$^2$; in other embodiments from about 5-100 mW/cm$^2$; in yet other embodiments from about 0.1-1.5 W/cm$^2$. In other embodiments, the acoustic energy applied through the energy delivery member may be a generally high intensity ultrasound of greater than about 1 W/cm$^2$ and less than about 25 kW/cm$^2$. In some embodiments, the acoustic energy applied through energy delivery member has an acoustic intensity from about 10 to about 1,000 W/cm$^2$; in some embodiments from about 1,000 to about 15,000 W/cm$^2$; and in yet other embodiments from about 3,000 to about 10,000 W/cm$^2$. The generally high intensity ultrasound may be sufficient to ablate tissue and/or cellular structures or debris, or it may be at a sub-ablation intensity that is sufficient to disrupt tissue and/or cellular structures or debris but not ablate. The pulse duration and repetition rate may be adjusted and matched to the frequency and intensity of acoustic energy pulses to achieve the desired effect.

The high frequency acoustic energy may be selectably activated on a continuous basis, or ultrasound energy may be applied, through the energy delivery member, on an intermittent basis, and the frequency and/or acoustic intensity may be adjustable and selectable by the operator. Operation of the ultrasound transducer at duty cycles of less than about 80% is generally preferred; in some embodiments at duty cycles of less than 50%; and in yet other embodiments at duty cycles of less than about 30%. Enhancement and/or coupling agents promoting and/or targeting acoustic energy deposition may be used and may be provided to a target site through the insertion member and/or the energy delivery member.

Handle 42, insertion wand 44 and energy delivery member 46, 48 may be provided in an integrated, single piece construction, or they may be provided as separate components that are detachable from one another. Handle 42 may be provided as a single- or multiple-use component. Insertion wands and/or energy delivery members may similarly be provided as integrated components or may be provided separately from one another, with appropriate interfaces for operation. Multiple configurations of insertion wands and/or energy delivery members may be provided for operation on common or multiple handles, with appropriate insertion wands and/or energy delivery members being selectable by a user depending on the circumstances of use. Insertion and energy delivery members may be provided as single- or multiple-use components, although they may generally be provided as sterile, disposable components that are mountable on a reusable handle. Device 40 may incorporate all of the components required for operation, or it may interface with a separate console, or control unit (not shown), that provides electrical power, liquid for infusion or aerosol delivery, operating control features, displays, and the like.

In some embodiments, devices of the type illustrated in FIGS. 6 and 7 are capable of selectively delivering high frequency acoustic energy, a liquid stream, aerosol particles and/or aerosol droplets, simultaneously or sequentially, in one or a plurality of delivery modes: continuous flow; intermittent flow; or high frequency pulsatile flow. Liquid, aerosol particles and/or aerosol droplets may be delivered from a common discharge port sequentially and intermittently, or from multiple, dedicated discharge ports, simultaneously or sequentially, and on a continuous or intermittent basis. Aspiration may be provided, additionally or alternatively, through one or more ports in the insertion wand and/or energy delivery member. Insertion wand 24 may be provided with one or more channels, or lumens, for delivery of liquids, aerosol particles, and/or aerosol droplets to a desired intranasal site, and for removal of material from the site by means of aspiration.

Controls may be provided on the device handle, as illustrated, or on an accessory device or module, allowing a user to select acoustic frequency and/or intensity, liquid and/or aerosol delivery modes, aspiration modes, visualization modalities, or the like. Controls may also be provided allowing a user to select from among various modes of operation or various pre-determined or pre-set operating modes. Devices of the present invention may thus be operated, manually or by selectable automated operation, in a single mode or multiple modes.

Figure 8A:
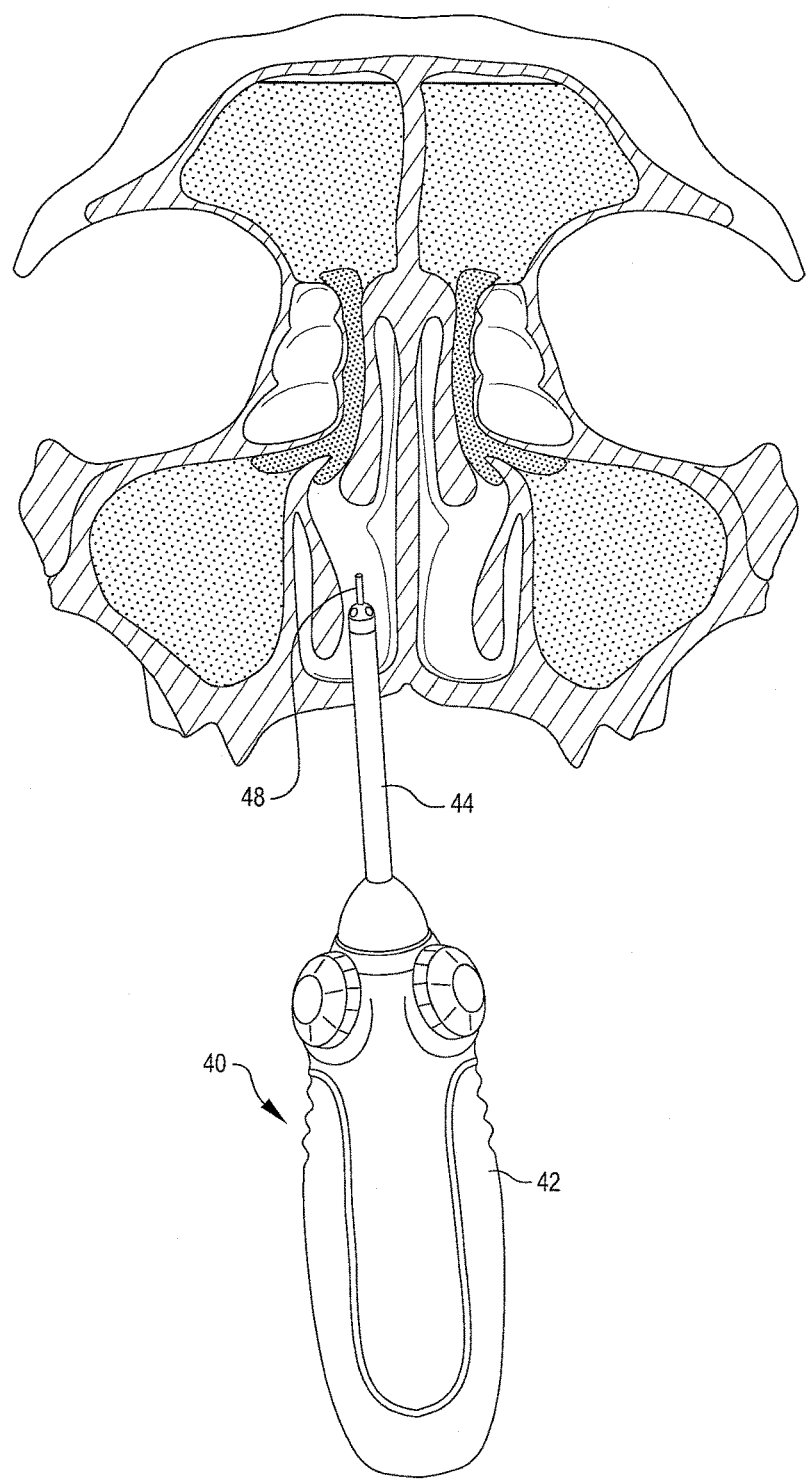
FIGS. 8A-8E show schematic diagrams illustrating the use of a device similar to that shown in FIGS. 6 and 7, with FIG. 8A showing insertion of the device into a nostril or sinus passage.
Figure 8B:
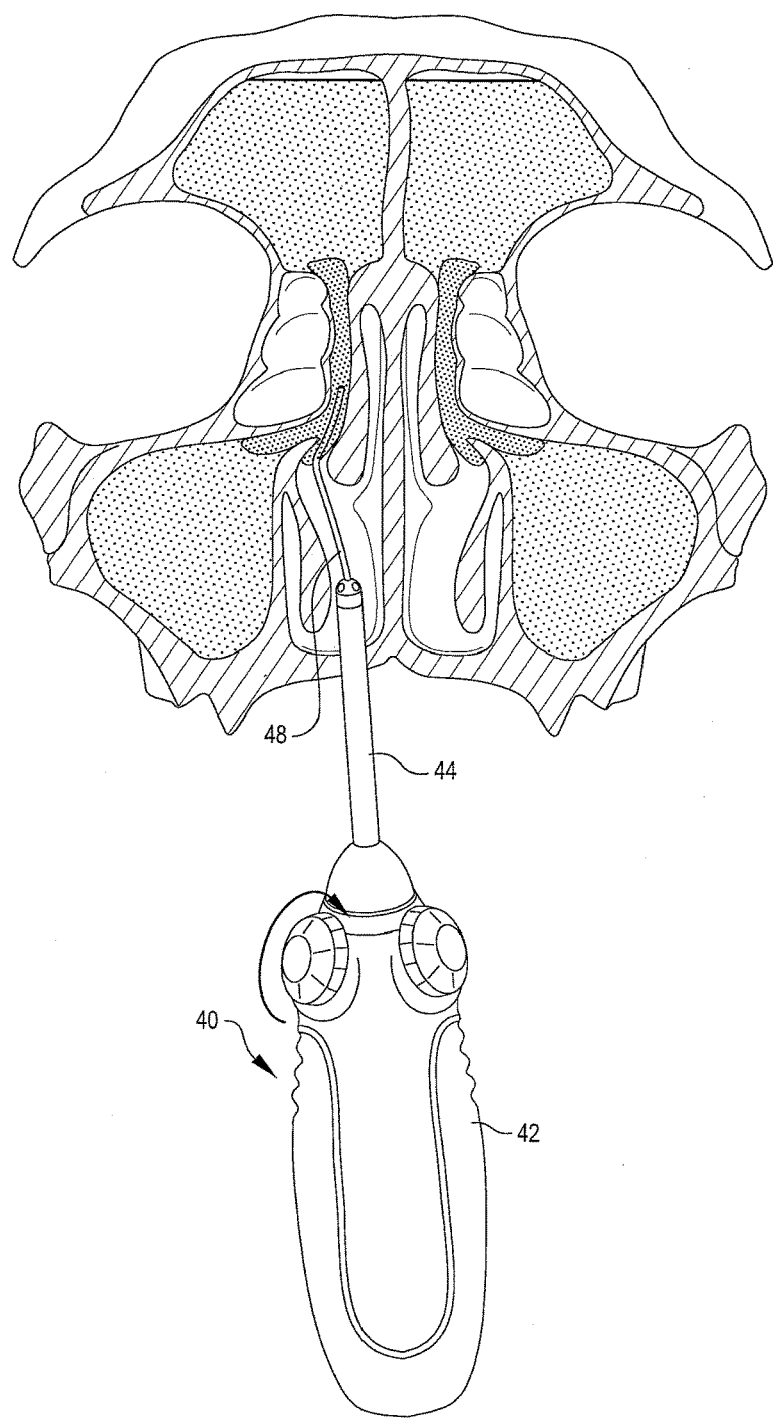
Figure 8C:
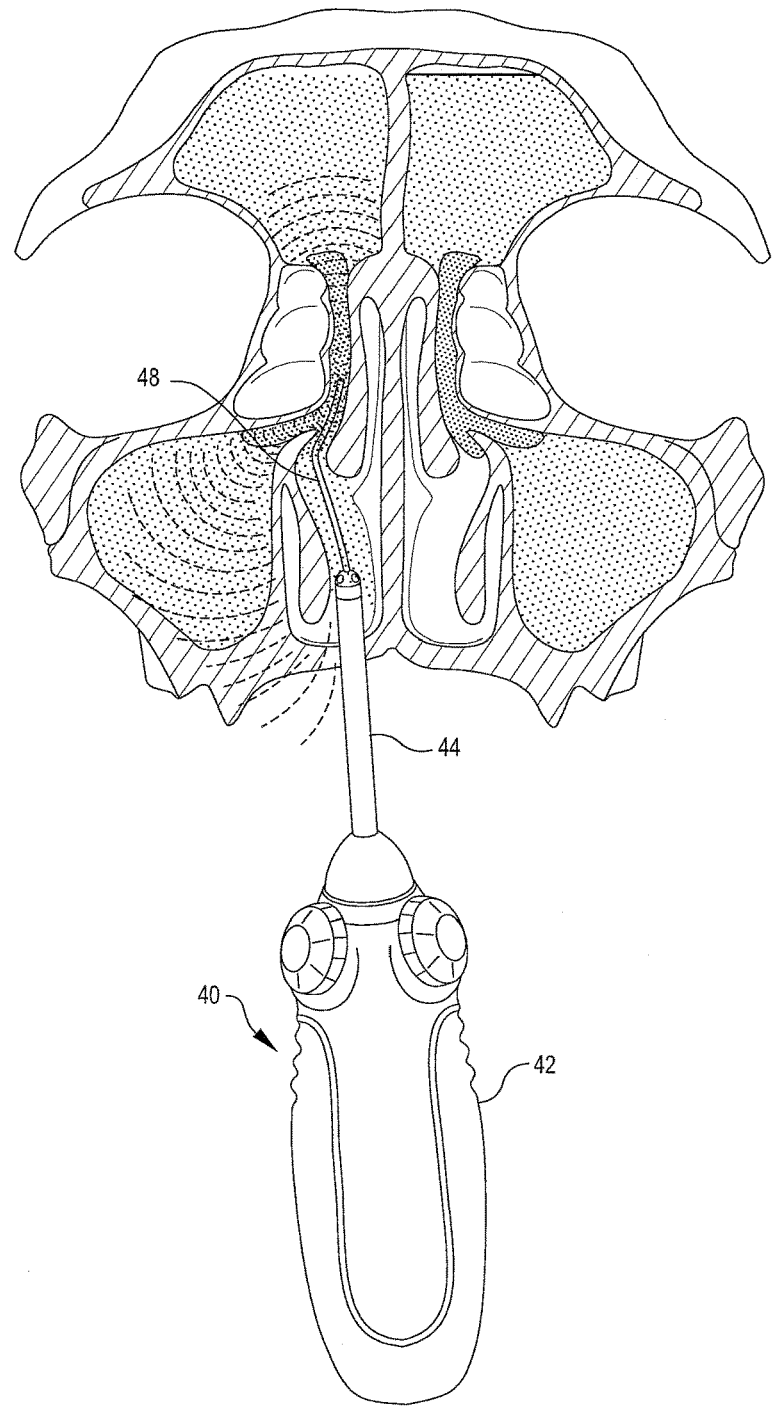
Figure 8D:
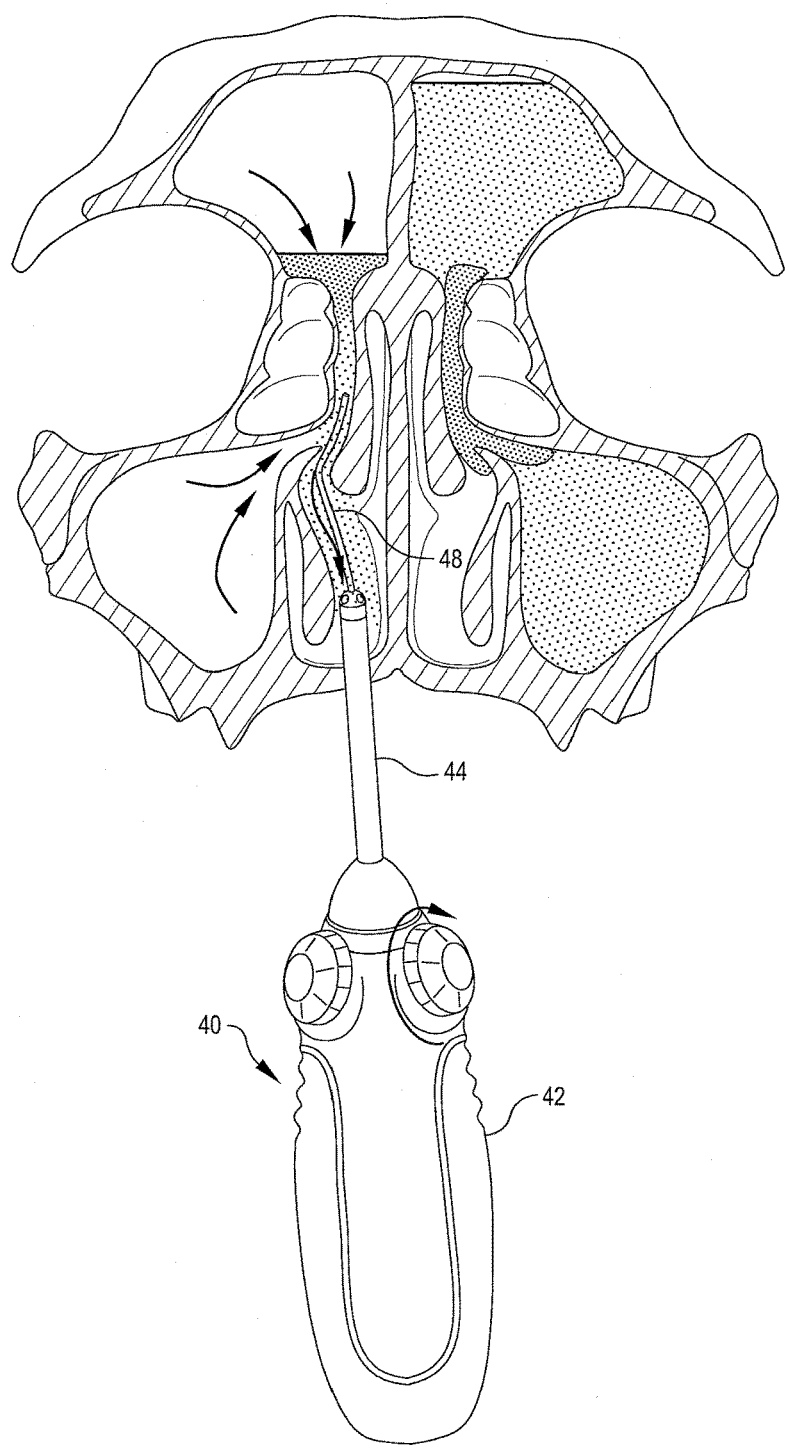
Figure 8E:
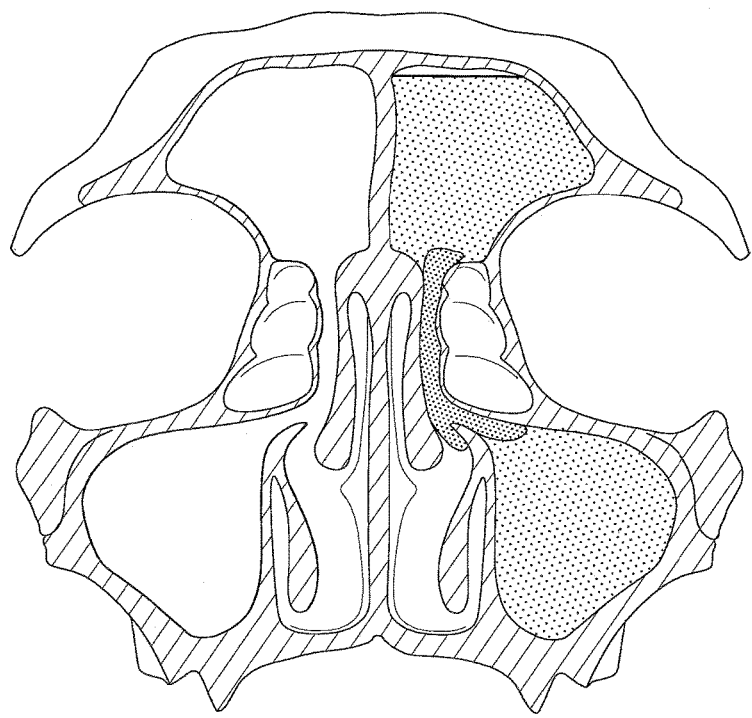

In one embodiment, schematically illustrated in FIGS. 8A-8E, a device 40 such as illustrated in and described with reference to FIGS. 6 and 7 may be operated in a high frequency acoustic energy deposition mode in which the insertion wand 44 and energy delivery member 48 are positioned in a nasal cavity, as shown in FIG. 8A. Energy delivery member 48 may be extended and guided, as shown in FIG. 8B, to contact mucus and/or debris forming an obstruction within the osteomeatal complex in nasal passageways. Acoustic energy delivery through delivery member 48 may be activated at a preset or selectable acoustic energy frequency and/or intensity to heat and/or cavitate and/or ablate mucus and/or debris forming the obstruction in the osteomeatal complex, as shown schematically in FIG. 8C. In another embodiment, the energy delivery member may be positioned to contact tissue and activated at preset or selectable acoustic energy frequency and/or intensity levels to heat and/or cavitate and/or ablate selected tissue sites.

Delivery of the high frequency and/or high intensity acoustic energy may be accompanied by infusion of liquids and/or aerosol particles or droplets. Loosened and extraneous materials may be aspirated during and/or following delivery of high frequency and/or high intensity acoustic energy and (optional) infusion of liquids and/or aerosol particles, as shown schematically in FIG. 8D to remove obstructions and clear passageways, leaving cleared passageways as illustrated schematically in FIG. 8E. In another embodiment, therapeutic light, such as ultraviolet light, may be emitted through a light transmissive portion of the energy delivery member and/or an associated wand prior to, during and/or following delivery of acoustic energy.

Figure 8F:
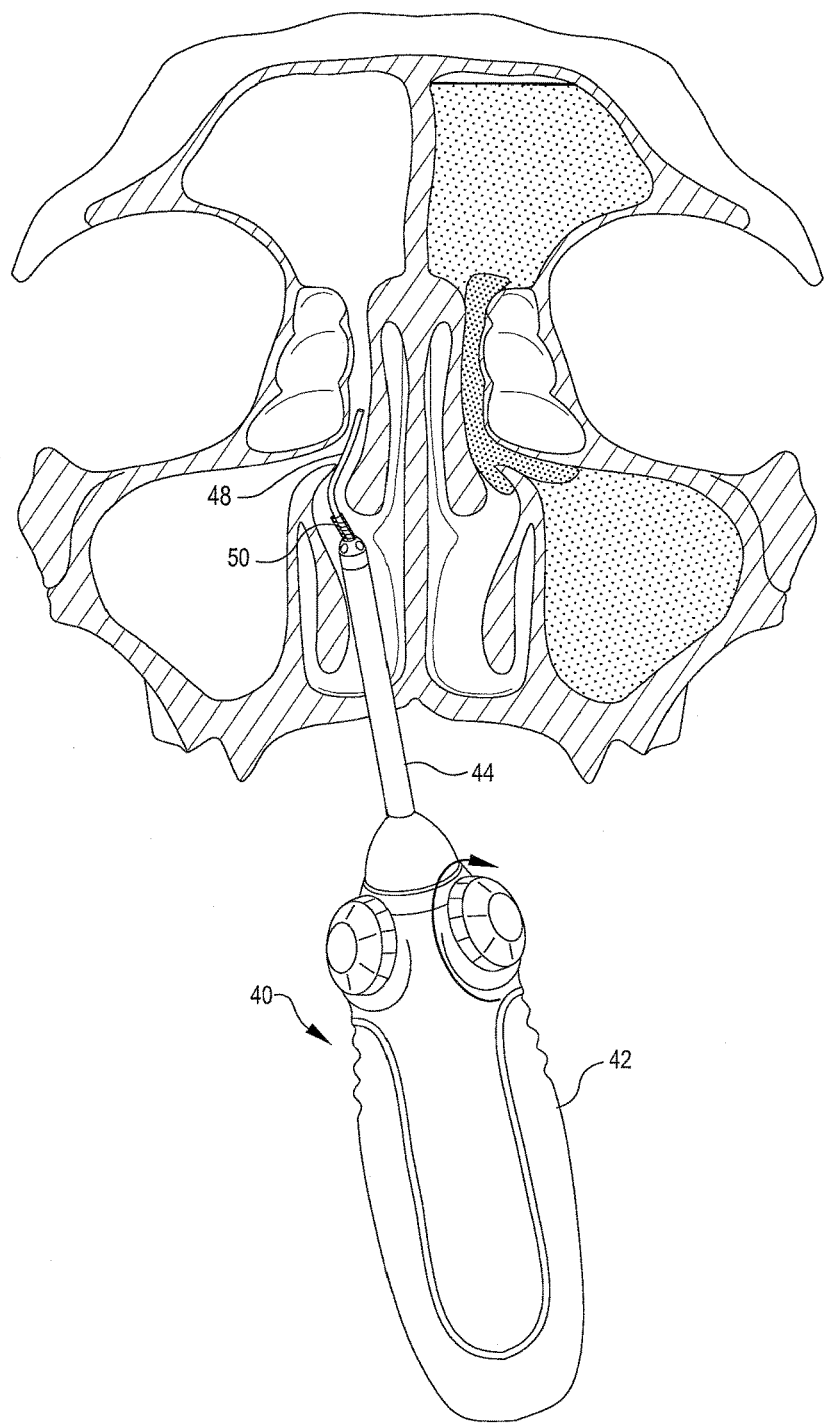
FIGS. 8F-8H show schematic diagrams illustrating the use of a device similar to that shown in FIGS. 6, 7 and 8A-D, modified to deploy a stent in an internal passageway after the passageway has been enlarged or cleared by delivery of acoustic energy delivered, for example, by the same device.
Figure 8G:
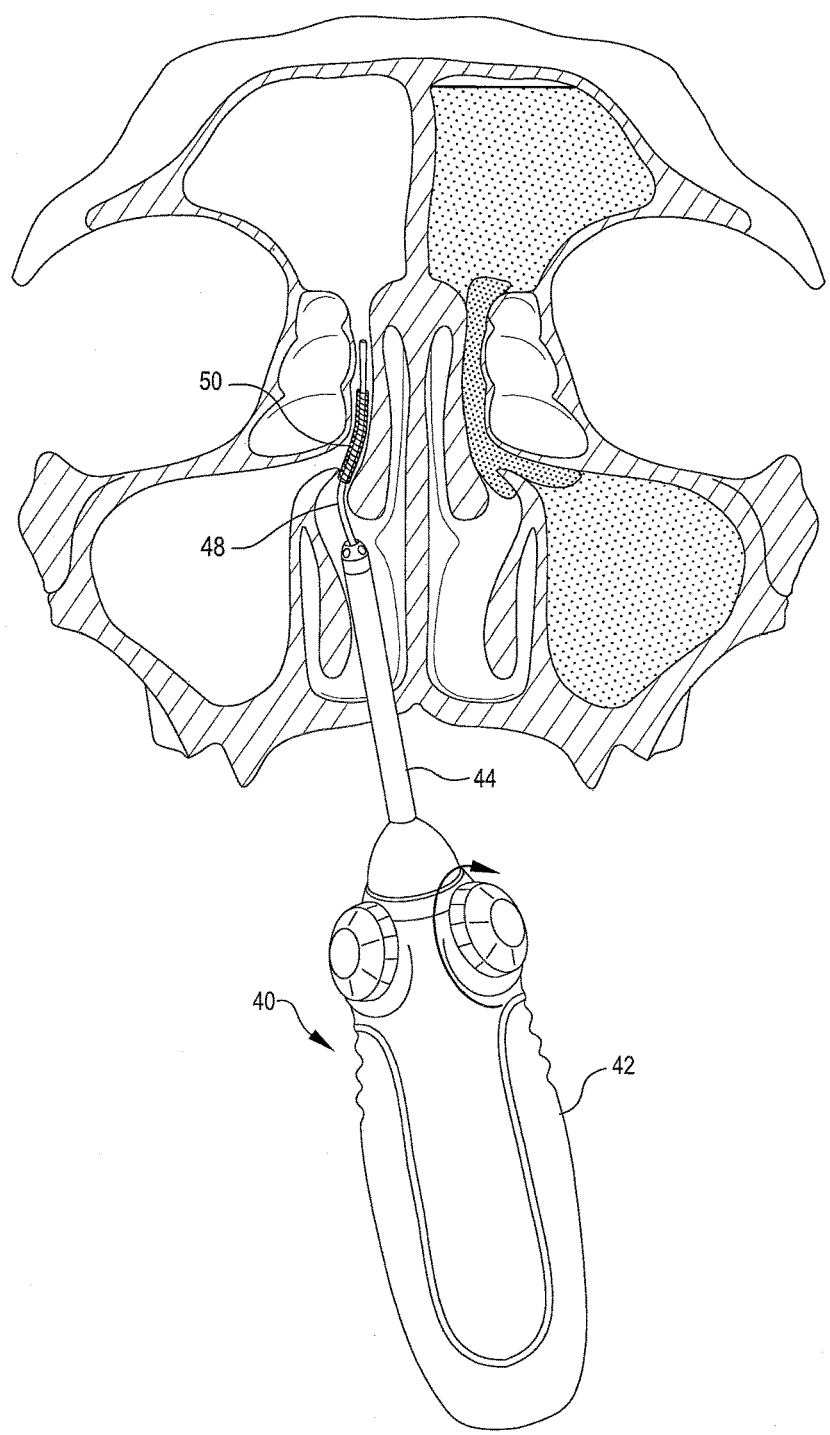
Figure 8H:
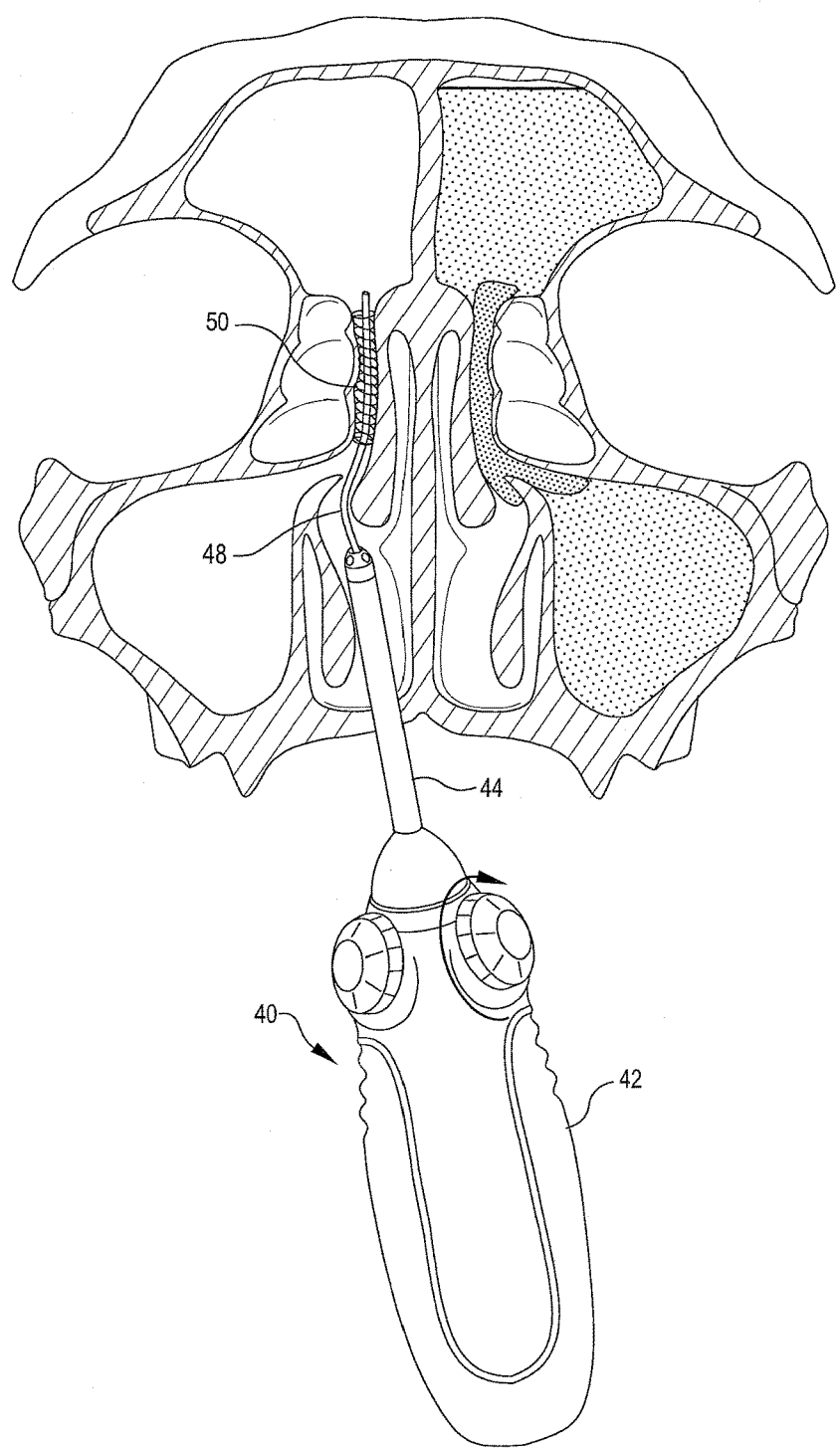

Delivery of an implantable device such as a stent to passageways previously cleared of obstructions using device 40, as schematically shown in FIGS. 8A-8E, may be desired to maintain the patency of cleared passageways. FIGS. 8F-8H illustrate another embodiment in which an implantable device, such as a stent, may be deployed using a system of the present invention. FIG. 8F schematically shows a stent 50 in a small diameter delivery condition being deployed from a distal end of insertion member 44 over energy delivery member 48. In some embodiments, an implantable device may be deployed over or guided to a placement site using energy delivery member 48; in alternative embodiments, an implantable device may be deployed using an alternative guidance and/or deployment system provided in connection with device 40. FIG. 8G illustrates advancement of implantable stent 50 toward the desired delivery site within the osteomeatal complex, still in the small diameter delivery condition, and FIG. 8H shows final placement of stent 50, now expanded to the larger diameter final placement condition, in the cleared passageway within the osteomeatal complex. Stents coated or otherwise associated with bioactive materials for delivery of the bioactive materials to surrounding tissue sites may be placed using systems of the present invention.

FIGS. 9A-9D illustrate yet another device embodiment of the present invention, in which a deformable and expandable member, such as an inflatable chamber 52, may be deployed using a system of the present invention. In one embodiment, a flexible, deformable bladder or inflatable chamber is constructed from a material having high acoustical transmission properties and is adapted for retaining an inflation medium such as an acoustically transmissive material comprising a liquid or gel-like substance within its interior volume for delivery of acoustic energy to a target site. In another embodiment, the inflatable chamber is constructed from a material that is light (e.g., UV) transmissive and is adapted for retaining an inflation medium having high light (e.g., UV) transmissive properties for delivery of light energy to the target site. In some embodiments, the inflatable chamber and the inflation medium may have both light and acoustic energy transmissive properties for delivery of both light energy and acoustic energy to the target site. In yet another embodiment, the inflatable chamber and/or the inflation medium may contain or be associated with one or more bioactive compositions such as, but not limited to, antibiotics, cancer therapeutic compositions, steroid compositions, and the like. In this embodiment, the bioactive composition(s) may be provided as a coating or may elute from the expandable member during use of the system.

The flexible, expandable chamber 52 may be stored in a collapsed condition within wand 44 and may be deployed and expanded at a target site by introduction of the liquid or gel-like inflation medium, as shown schematically in FIGS. 9A-9D.

Figure 9A:
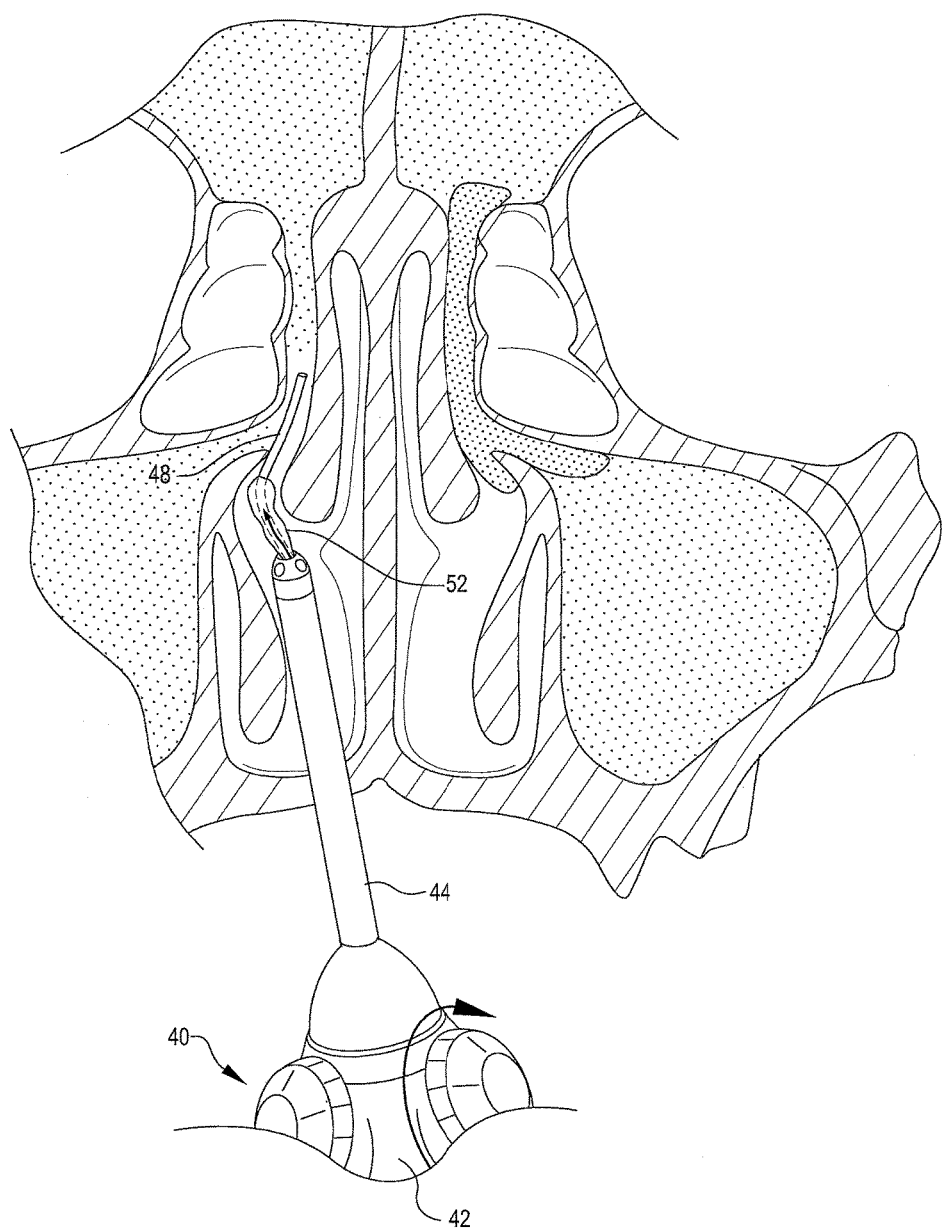
FIGS. 9A-9D show schematic diagrams illustrating the use of a device similar to that shown in FIGS. 6, 7 8A-D, modified to deploy an expandable member, such as a balloon, over a guide member.
Figure 9B:
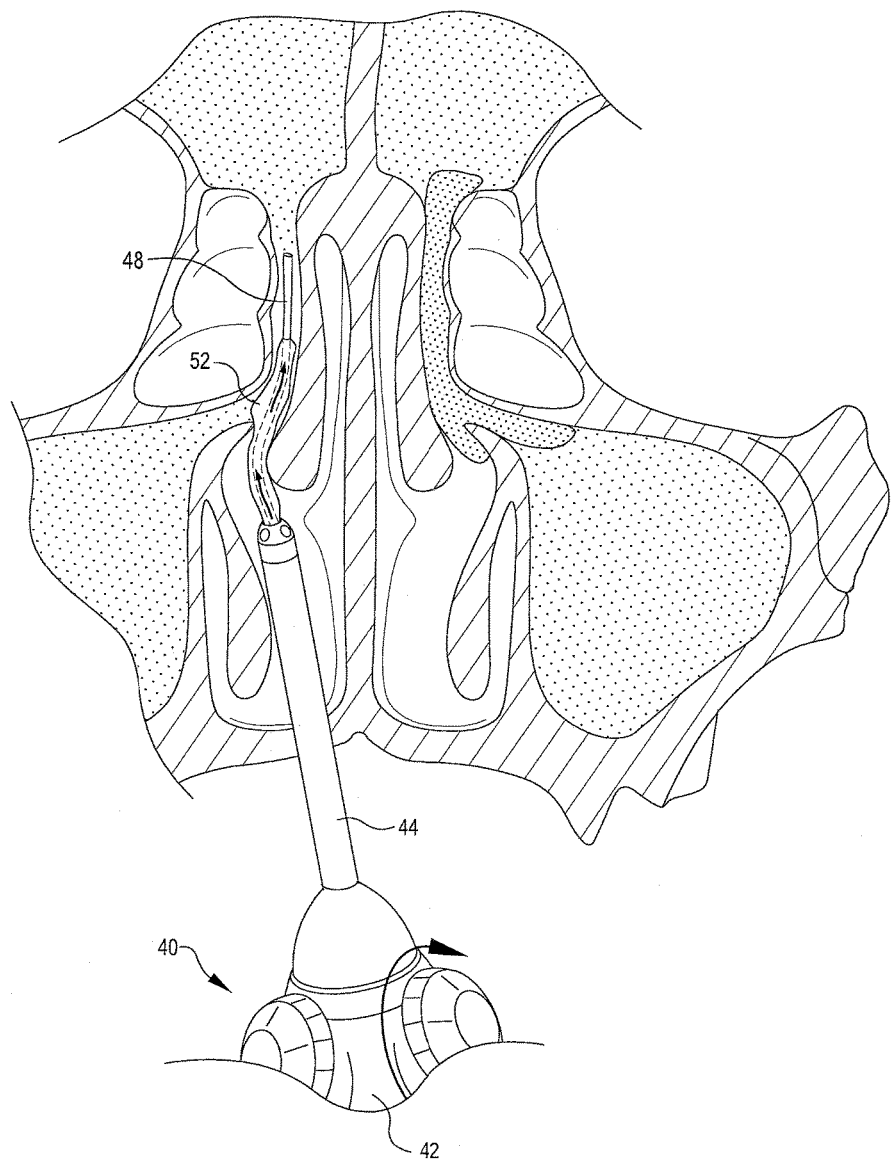
Figure 9C:
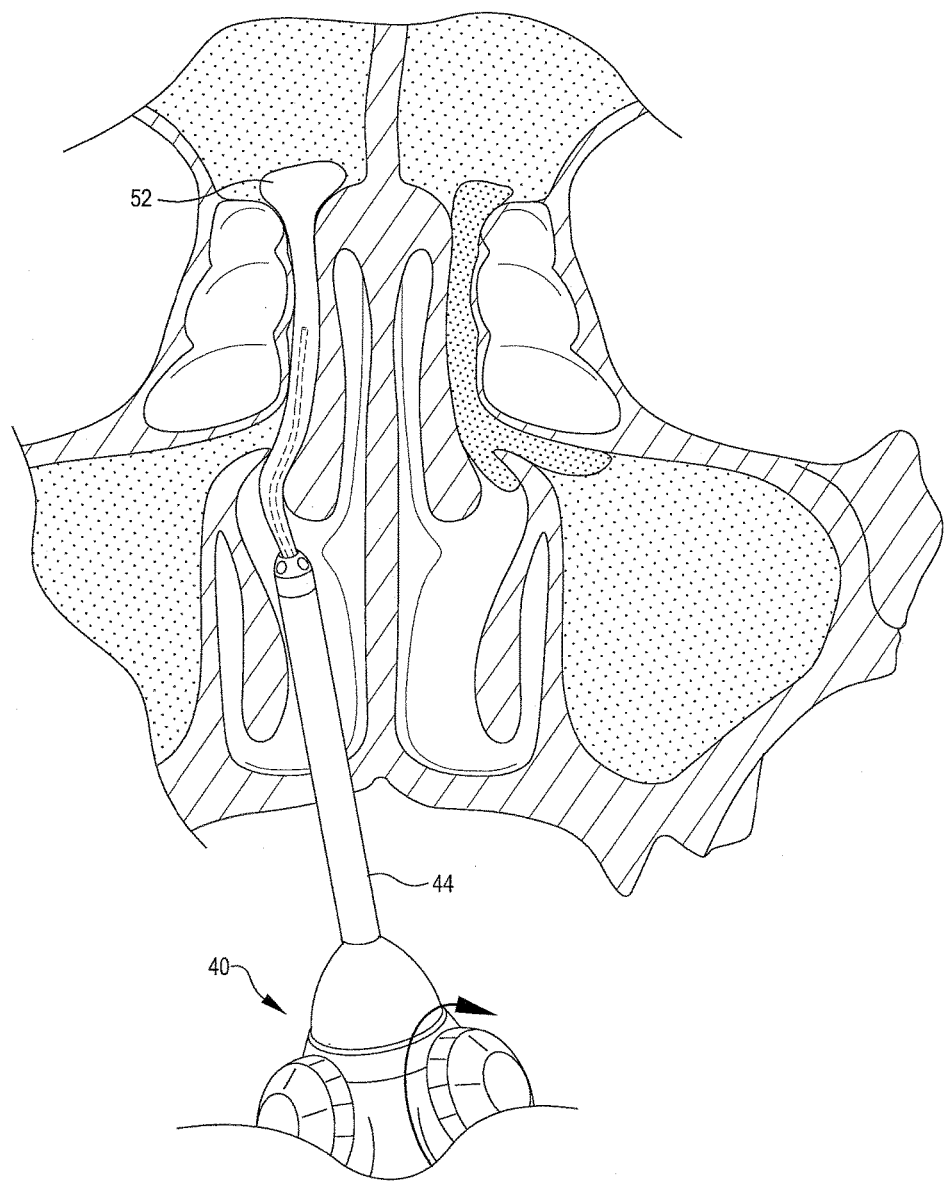
Figure 9D:
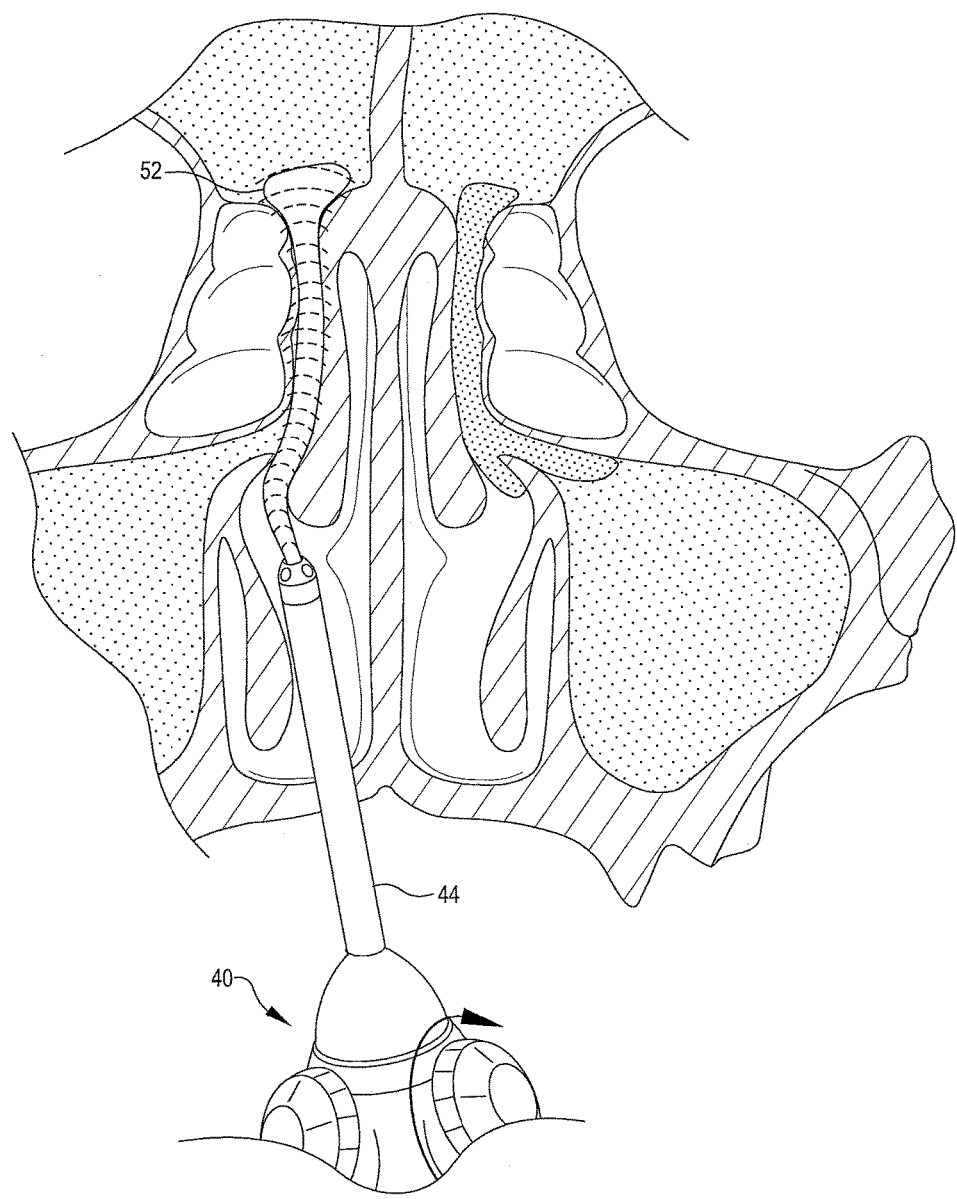

FIGS. 9A-9D illustrate deployment of expandable chamber 52 over energy delivery member 48, which also serves as a guide for deployment of the expandable chamber. In alternative embodiments, an expandable chamber may be deployed using an alternative guidance and/or deployment system provided in connection with device 40. FIG. 9A schematically shows expandable chamber 52 being deployed from a distal end of insertion member 44 over energy delivery member 48. FIG. 9B schematically shows expandable chamber 52 being further deployed and guided through an internal passageway by energy delivery member 48. FIG. 9C schematically shows expandable chamber 52 in an exemplary fully deployed condition in which it encloses and extends beyond energy delivery member 48, substantially contacting the internal passageway walls and extending into a distal internal cavity. FIG. 9D schematically illustrates application of energy, such as ultrasound energy, through the inflation medium, thereby providing delivery of energy, such as ultrasound energy, to tissues contacting the expandable chamber, and to neighboring tissues as well. Energy delivery parameters and features as described above in connection with the description of FIGS. 5A-5C are exemplary and may be used with the system and method embodiments described above.

In some embodiments, multiple pulsating liquid rinse and aerosol delivery options, as well as multiple energy deposition options, may be programmed in the device, with various operating programs being predetermined and selectable by the user. In alternative embodiments, a user may select pulsating liquid rinse, aerosol delivery and/or energy deposition options by means of multiple selectable actuators. In any of these embodiments, multiple and selectable modes may be implemented, whereby programmed or selectable levels of liquid and/or aerosol flow or volume, aerosol particle and/or droplet size, aerosol particle and/or droplet density, pulsation frequency, temperature, acoustic energy frequency, intensity, pulse repetition rate, duty cycle, and the like, may be selectable by the user.

Devices of the present invention may be provided as an integral unit that may be used once or several times and then disposed of, or an integral device may be reused on a to frequent basis. Alternatively, as described above, the handle and nostril interface member or delivery wand may be detachable from one another. In a multiple component embodiment, the handle may be provided as a reusable component, while the detachable nostril interface member or delivery wand may be provided as a reusable or disposable element. Single or multiple use "covers" may be provided for covering the nostril interface member or the delivery wand, providing replaceable sterile, or antiseptic surfaces for contacting the nose and nasal passages. Such covers may be flexible and resilient and generally match the outer configuration of the nostril interface member and/or delivery wand, so that they may be mounted on and closely fitted over the interface member or delivery wand for multiple uses/multiple users, and the like.

Specific embodiments of methods and devices described herein with reference to use in intranasal areas such as nasal passages, sinuses and sinus ostia and these methods and devices may be used, for example, for treating common colds, nasal congestion and allergic rhinitis, as well as sinusitis and other nasal conditions. They may be used for treatment of acute or chronic conditions, and they may be used on a frequent basis to cleanse intranasal passages, thereby reducing bacterial infection and the incidence of nasal congestion, colds, sinusitis and the like.

The methods and devices described herein are also suitable for treating pathologies at other tissue sites that would benefit from biofilm dissolution, reduction in inflammation, reversal of mechanical obstruction(s), reversal of hypertrophy, improvement of poor circulation, repair of dysfunctional immune responses, repair of dysfunctional immune modulation, removal of infection, and reversal of dysfunctional cell proliferation, death or ablation. Methods and devices of the present invention embodied in interventional catheter systems may, for example, be adapted for use in blood vessels, air passageways, the gastrointestinal tract, the genitourinary tract (e.g., urethra, bladder, ureters, renal calyxes, and the like) and other internal cavities and passageways.

In particular, methods and devices of the present invention as embodied in interventional catheters may be used to deliver liquids to internal body sites using a generally high frequency (sonic and/or ultrasonic) pulsatile flow. Interventional catheters of the present invention may also be adapted to deliver energy, such as acoustic and/or light energy, to tissue sites located in various parts of the body to address the following exemplary pathologies:

pathologies of the cardiovascular system-such as atheroscerlosis, thromboses, ectopic cardiac pacing sites, valve lesions, cardiac muscle lesions, aneurysms, intra-chamber emboli, intra-vascular emboli, and pathologies of the gastrointestinal tract-such as obstructions, bezoars, strictures, cancers, hypertrophies, liver necrosis, liver masses, splenic abscesses, pancreatic tumors, pancreatic masses, pancreatic abscesses, and pathologies of the genitourinary system-such as nephrolithiases, constrictures, fibroids, cervical cancer, abscesses, patent fallopian tubes, non-patent fallopian tubes, ovarian cysts, testicular masses, hydronephrosis, and pathologies of the nervous system-such as brain abscesses, brain tumors, spinal cord abscesses, spinal cord tumors, dysfunctional nerve transmission, blood clots in and around the nerves, necrotic tissue in and around the nerves, and pathologies of the musculoskeletal system-such as injured menisci, injured tendons and ligaments, degenerated intervertebral discs, chronic back pain (ablation of pain source nerves), infected joints, infected bones, arthritic joints (removal of degenerated material and US-stimulation of chondrocytes, poorly growing fractured bones (US stimulation of osteoblasts), and pathologies of the dermatologic system-such as subcutaneous abscesses, chronic skin infections, eczema, chronic fungal infections (skin and nails).

Figure 10A:
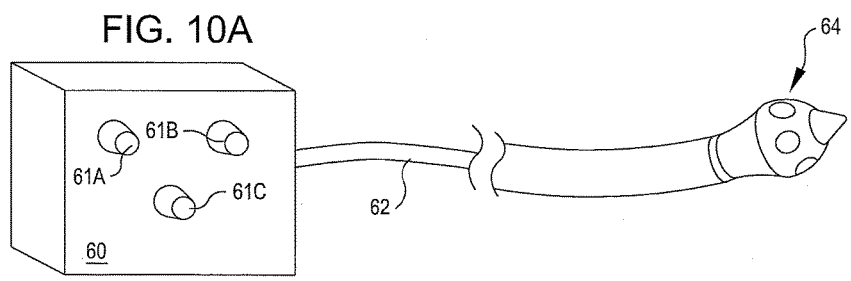
FIGS. 10A-10C show highly schematic diagrams illustrating interventional catheter-based systems of the present invention for accessing internal tissue sites, such as blood vessels, air passageways, the gastrointestinal and genitourinary tracts, and the like, which are not conveniently accessible through a natural orifice.
Figure 10B:
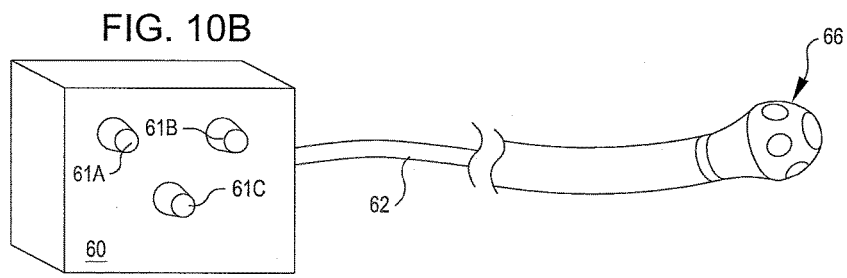
Figure 10C:
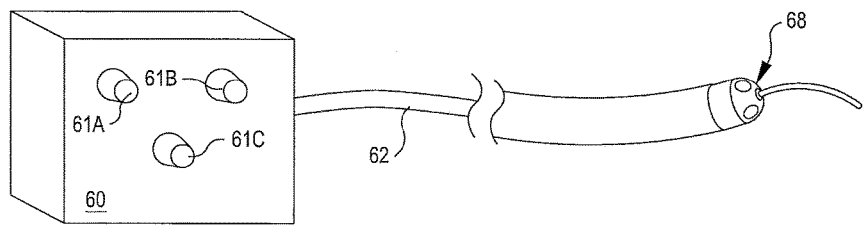

FIGS. 10A-10C show highly schematic diagrams illustrating interventional catheter-based devices of the present invention. FIGS. 10A-C show a controller 60 housing, or in operable communication with energy delivery systems (such as acoustic and/or light-based energy delivery systems), liquid delivery systems, aspiration systems, and the like, and having exemplary selectable control operators 61A, 61B and 61C for operating energy delivery systems, liquid delivery systems, aspiration systems, etc. Suitable systems, control features and selectable control operators are well known in the art and are not described in detail herein.

FIGS. 10A-10C each illustrate a catheter 62 exiting controller 60 at a proximal end and having an operating head 64, 66, 68 located at or near a distal end of the catheter. The catheter may be adapted for introduction to and guidance through various types of body lumens and passageways; many catheter systems are known in the art and are suitable for use in different body lumens and passageways. Catheter-based systems of the present invention may be designed for use with or without a guide wire or another guidance system, and may be guided using remotely operated (e.g., robotic) guidance systems.

FIG. 10A schematically shows an operating head 64 of the type shown and described above with reference to FIG. 3. Operating head 64 may be employed for delivery of a liquid or aerosol stream from one or more discharge ports(s) at one or more pulsatile frequencies and/or energies, as described above. Operating head 64 may also incorporate an energy delivery member for delivering generally high frequency and/or high intensity ultrasound energy, alone or in combination with another treatment modality such as administration of an antimicrobial or therapeutic agent, application of electromagnetic radiation (e.g., UV light), an electrical field, radio frequency energy, laser energy, microwave energy, or the like.

FIG. 10B schematically shows an operating head 66 of the type shown in FIGS. 5A-5C. This operating head may perform any of the functions described with reference to operating head 64, described above, and may additionally comprise an energy delivery member in the form of a controllably expandable chamber for contacting tissue in oddly shaped and unevenly contoured cavities and passageways. The expandable chamber may be filled with an energy transmissive material, such as an acoustically and/or light transmissive material, for delivery of acoustic energy and/or light energy to tissue surfaces forming cavity and passageway walls, as described above. The expandable chamber may also be employed for delivery of a bioactive composition, such as a drug or another agent, prior to, during or following deployment of the expandable chamber, also as described above.

FIG. 10C schematically shows an operating head 68 of the type shown in FIGS. 7, 8A-8D, 8F-8H, and 9-9D. This operating head may perform any of the functions described with reference to operating heads 64 and 66, described above, and is additionally provided with an acoustic energy delivery member that is extendible and retractable to deliver energy, such as acoustic and/or light energy, to an internal target site. Operating head 64 may also incorporate an energy delivery member for delivering generally high frequency and/or high intensity ultrasound energy, alone or in combination with another treatment modality such as administration of an antimicrobial or therapeutic agent, application of electromagnetic radiation (e.g., UV light), an electrical field, radio frequency energy, laser energy, microwave energy, or the like.

It will be appreciated that the methods and systems of the present invention may be embodied in a variety of different forms, and that the specific embodiments shown in the figures and described herein are presented with the understanding that the present disclosure is considered exemplary of the principles of the invention, and is not intended to limit the invention to the illustrations and description provided herein. Accordingly, the descriptions provided above are considered as being illustrative and exemplary of specific structures, aspects and features within the broad scope of the present invention and not as limiting the scope of the invention.

We claim:

1. A system for delivery of high frequency acoustic energy to a target site at a tissue or at an obstruction within a body cavity or lumen, comprising:
   an insertion wand sized and configured for insertion into a body cavity or lumen;
   an acoustic energy delivery member associated with the insertion wand for contacting tissue and conveying high frequency acoustic energy directly to the target site, a distal end of the insertion wand having a plurality of ports, including a fluid delivery port and an aspiration port, circumscribing a central portion of the distal end; and
   a fluid source that delivers fluid via the fluid delivery port to the target site in a pulsatile flow,
   wherein the acoustic energy delivery member includes a wire member that delivers acoustic energy extendable from the central portion of the distal end of the insertion wand to a position external to the insertion wand and distal to the plurality of ports.

2. The system of claim 1, wherein the acoustic energy delivery member is adapted to deliver generally high frequency sonic and/or ultrasonic acoustic energy or high intensity ultrasound (HIU) or high intensity focused ultrasound (HIFU) to the target site.

3. The system of claim 1, wherein the acoustic energy delivery member further includes a flexible, expandable member adapted to be expanded at the target site upon by filling with an acoustically transmissive material.

4. The system of claim 3, wherein the flexible, expandable member is fluid permeable.

5. The system of claim 1, wherein the insertion wand is sized and configured for insertion into at least a portion of a nasal or sinus cavity.

6. The system of claim 1, wherein the insertion wand is sized and configured for insertion into at least a portion of a vascular system, a respiratory system, a gastrointestinal system, a reproductive system, or a natural orifice.

7. The system of claim 1, wherein the system additionally incorporates a system for collection of material removed by aspiration.

8. The system of claim 1, wherein the system is adapted to provide delivery of one or more sequences of acoustic energy, with each sequence providing delivery of acoustic energy at a different frequency, intensity, pulse duration, pulse repetition rate, or duty cycle.

9. The system of claim 8, wherein multiple sequences are programmed in the system as multiple programmed protocols selectable by a user.

10. The system of claim 1, additionally comprising a visualization system for visualization of the target site.

11. The system of claim 1, additionally comprising an illumination system for illumination of a target site.

12. The system of claim 1, additionally comprising an endoscopic port for delivery of tools or agents to the target site.

13. A method for delivering high frequency acoustic energy to a target site, comprising positioning an insertion wand in proximity to the target site, a distal end of the insertion wand having a plurality of ports, including a fluid delivery port and an aspiration port, circumscribing a central portion of the distal end; positioning an acoustic energy delivery member associated with the insertion wand at the target site in contact with tissue; applying high frequency acoustic energy directly to the target site through the acoustic energy delivery member; and delivering fluid to the target site via the fluid delivery port using a pulsatile flow, wherein the acoustic energy delivery member includes a wire member that delivers high frequency acoustic energy and is extendible from the central portion of the distal end of the insertion wand to a position external to the insertion wand and distal to the plurality of ports, and positioning the acoustic energy delivery member at the target site includes extending the wire member from the insertion wand.

14. The method of claim 13, comprising applying high frequency sonic or ultrasonic energy or high intensity ultrasound (HIU) or high intensity focused ultrasound (HIFU) to the target site.

15. The method of claim 13, wherein the acoustic energy delivery member further includes a flexible, expandable member and positioning the acoustic energy delivery member at the target site includes expanding the flexible, expandable member at the target site by filling it with an acoustically transmissive material.

16. The method of claim 15, comprising expanding the flexible, expandable member at the target site to a sufficient degree that an external surface of the expandable member contacts tissue at the target site.

17. The method of claim 16, additionally comprising delivering acoustic energy through the acoustically transmissive material and the external surface of the expandable member to tissue at the target site.

18. The method of claim 17, comprising delivering acoustic energy through the acoustically transmissive material and the external surface of the expandable member using the wire member extendible from the insertion wand and into an internal volume of the expandable member.

19. The method of claim 17, additionally comprising delivering a bioactive composition associated with the expandable member prior to or during delivery of acoustic energy.

20. The method of claim 13, additionally comprising converting fluid into aerosol and delivering the aerosol to the target site.

21. The method of claim 20, wherein the pulsatile flow is characterized by pulsations having a frequency of greater than 1500 Hz.

22. The method of claim 13, additionally comprising aspirating material from the target site.

23. The method of claim 13, comprising delivering one or more sequences of acoustic energy, with each sequence providing delivery of acoustic energy at a different frequency, intensity, pulse duration, pulse repetition rate, or duty cycle.

24. The method of claim 13, comprising positioning the acoustic energy delivery member at a target site incorporating an internal passageway and deploying an implantable device in the internal passageway following application of high frequency acoustic energy to the target site.

25. The system of claim 1, further comprising an aerosol generator that converts fluid supplied by the fluid source into aerosol for delivery to tissue site through the fluid delivery port.

\* \* \* \* \*